US012171962B2

(12) United States Patent
Gianotti et al.

(10) Patent No.: US 12,171,962 B2
(45) Date of Patent: *Dec. 24, 2024

(54) MECHANICALLY ACTUATED AND FUNCTIONALLY INTEGRATABLE CATHETER SYSTEM FOR TREATING VASCULAR AND NON-VASCULAR DISEASES AND RELATED METHODS

(71) Applicant: BIOTRONIK AG, Buelach (CH)

(72) Inventors: Marc Gianotti, Wiesendangen (CH); Ulf Fritz, Tengen (DE); Dragana Gajic, Stetten (CH)

(73) Assignee: BIOTRONIK AG, Buelach (CH)

( * ) Notice: Subject to any disclaimer, the term of this patent is extended or adjusted under 35 U.S.C. 154(b) by 1118 days.

This patent is subject to a terminal disclaimer.

(21) Appl. No.: 16/930,632

(22) Filed: Jul. 16, 2020

(65) Prior Publication Data

US 2021/0001096 A1    Jan. 7, 2021

Related U.S. Application Data

(63) Continuation-in-part of application No. 15/744,027, filed as application No. PCT/EP2016/050375 on Jan. 11, 2016, now Pat. No. 10,758,717.

(Continued)

(51) Int. Cl.
*A61M 25/10*     (2013.01)
*A61M 25/00*     (2006.01)

(52) U.S. Cl.
CPC ...... *A61M 25/104* (2013.01); *A61M 25/0097* (2013.01); *A61M 25/1025* (2013.01);
(Continued)

(58) Field of Classification Search
CPC ...... A61M 2025/0681; A61M 25/0097; A61M 2025/0004; A61M 2025/1052;
(Continued)

(56) References Cited

U.S. PATENT DOCUMENTS 3,045,677 A    7/1962   Wallace
4,323,071 A *  4/1982   Simpson ........... A61M 25/1036
                                                  604/920

(Continued)

FOREIGN PATENT DOCUMENTS

CN         1822872 A       8/2006
CN      100544787 C        9/2009
(Continued)

*Primary Examiner* — Katherine M Shi
(74) *Attorney, Agent, or Firm* — Greer, Burns & Crain, Ltd.; Steven P. Fallon

(57) ABSTRACT

A functionally integratable catheter system comprising functional units that can be assembled to produce different configurations. The functional units include: one or more FICS support catheters; one or more FICS dilators: one or more FICS PTA catheters; and one or more FICS lock-grip handles. Functional units can be provided in a pre-assembled form by the manufacturer, optionally pre-packaged as a device tray, for assembly into different configurations by clinical operators. The configurational adaptability of the FICS platform enables physicians to efficiently address multiple procedural aspects of treatment processes, including lesion access, lesion penetration, guide-wire negotiation, lesion recanalization, and dilation, by providing in situ treatment options, including intraluminal and/or extraluminal recanalization, and enables multi-stage, patient-customized treatments of complex lesions in vivo, including lesion-length-selective, multi-stage angioplasty treatment.

22 Claims, 15 Drawing Sheets

Related U.S. Application Data

(60) Provisional application No. 62/191,517, filed on Jul. 13, 2015.

(52) U.S. Cl.
CPC .............. *A61M 2025/0004* (2013.01); *A61M 2025/1068* (2013.01)

(58) Field of Classification Search
CPC ............ A61M 25/0136; A61M 25/104; A61M 2025/09175; A61M 2025/09183; A61M 2025/1047; A61M 25/10; A61M 25/1011; A61M 25/1018; A61M 29/00; A61B 2017/22048; A61B 2017/22051; A61B 2017/2206

See application file for complete search history.

(56) References Cited

U.S. PATENT DOCUMENTS

| | | |
|---|---|---|
| 4,447,227 A | 5/1984 | Kotsanis |
| 4,564,014 A | 1/1986 | Fogarty et al. |
| 4,762,130 A | 8/1988 | Fogarty et al. |
| 4,763,654 A | 8/1988 | Jang |
| 4,771,777 A * | 9/1988 | Horzewski ......... A61M 25/1011 604/101.05 |
| 4,921,483 A | 5/1990 | Wiljay et al. |
| 4,983,167 A | 1/1991 | Sahota |
| 5,002,532 A | 3/1991 | Gaiser et al. |
| 5,019,042 A | 5/1991 | Sahota |
| 5,035,686 A | 7/1991 | Crittenden et al. |
| 5,071,406 A | 12/1991 | Jang |
| 5,147,377 A | 9/1992 | Sahota |
| 5,246,421 A | 9/1993 | Saab |
| 5,263,963 A | 11/1993 | Garrison et al. |
| 5,383,856 A | 1/1995 | Bersin |
| 5,395,333 A | 3/1995 | Brill |
| 5,409,460 A | 4/1995 | Krumme |
| 5,415,635 A | 5/1995 | Bagaoisan et al. |
| 5,423,846 A | 6/1995 | Fischell |
| 5,466,230 A | 11/1995 | Davila |
| 5,470,313 A | 11/1995 | Crocker et al. |
| 5,484,411 A | 1/1996 | Inderbitzen et al. |
| 5,549,551 A | 8/1996 | Peacock et al. |
| 5,645,529 A | 7/1997 | Fagan et al. |
| 5,681,343 A | 10/1997 | Miller |
| 5,716,340 A | 2/1998 | Schweich et al. |
| 5,843,092 A | 12/1998 | Heller et al. |
| 5,951,514 A | 9/1999 | Sahota |
| 5,961,536 A | 10/1999 | Mickley et al. |
| 6,022,359 A | 2/2000 | Frantzen |
| 6,126,634 A | 10/2000 | Bagaoisan et al. |
| 6,506,178 B1 | 1/2003 | Schubart et al. |
| 6,527,741 B1 | 3/2003 | Lee et al. |
| 6,595,959 B1 | 7/2003 | Sratienko |
| 6,695,863 B1 | 2/2004 | Ramzipoor et al. |
| 6,719,772 B2 | 4/2004 | Trask et al. |
| 6,884,257 B1 | 4/2005 | Cox |
| 6,979,342 B2 | 12/2005 | Lee et al. |
| 7,141,059 B2 | 11/2006 | Duchamp et al. |
| 7,322,957 B2 | 1/2008 | Kletschka et al. |
| 7,556,634 B2 | 7/2009 | Lee et al. |
| 7,575,568 B2 | 8/2009 | Holman et al. |
| 7,708,931 B2 | 5/2010 | Schaeffer et al. |
| 7,713,233 B2 | 5/2010 | Burgmeier et al. |
| 7,722,568 B2 | 5/2010 | Lenker et al. |
| 7,744,973 B2 | 6/2010 | Schoenle et al. |
| 7,906,066 B2 | 3/2011 | Wilson et al. |
| 7,942,850 B2 | 5/2011 | Levit et al. |
| 8,048,032 B2 | 11/2011 | Root et al. |
| 8,070,719 B2 | 12/2011 | Lee |
| 8,257,382 B2 | 9/2012 | Rottenburg et al. |
| 8,257,383 B2 | 9/2012 | Rottenburg et al. |
| 8,303,537 B2 | 11/2012 | Holman et al. |
| 8,382,738 B2 | 2/2013 | Simpson et al. |
| 8,382,786 B2 | 2/2013 | Besselink et al. |
| 8,388,602 B2 | 3/2013 | Wilson et al. |
| 8,425,549 B2 | 4/2013 | Lenker et al. |
| 8,444,608 B2 | 5/2013 | Haslinger et al. |
| 8,613,722 B2 | 12/2013 | Lee et al. |
| 8,684,963 B2 | 4/2014 | Qiu et al. |
| 8,721,624 B2 | 5/2014 | Wilson et al. |
| 8,740,961 B2 | 6/2014 | Fulton, III |
| 9,050,441 B2 | 6/2015 | Solar et al. |
| 9,056,190 B2 | 6/2015 | Simpson et al. |
| 9,061,119 B2 | 6/2015 | Le et al. |
| 9,168,359 B2 | 10/2015 | Rowe et al. |
| 9,205,223 B2 | 12/2015 | Wilson et al. |
| 9,326,756 B2 | 5/2016 | Stangenes et al. |
| 9,327,101 B2 | 5/2016 | Gianotti et al. |
| 9,352,129 B2 | 5/2016 | Nardeo et al. |
| 9,364,642 B2 | 6/2016 | Sina |
| 9,381,325 B2 | 7/2016 | Haslinger et al. |
| 9,474,882 B2 | 10/2016 | Franklin |
| 9,539,368 B2 | 1/2017 | Haslinger et al. |
| 9,623,216 B2 | 4/2017 | Gianotti |
| 9,669,196 B2 | 6/2017 | Lee et al. |
| 9,707,380 B2 | 7/2017 | Qiu et al. |
| 9,867,967 B2 | 1/2018 | Gianotti et al. |
| 9,968,713 B2 | 5/2018 | Simpson et al. |
| 10,045,785 B2 | 8/2018 | Bernier et al. |
| 10,080,868 B2 | 9/2018 | Sina |
| 10,130,798 B2 | 11/2018 | Pigott |
| 10,173,032 B2 | 1/2019 | Suzuki |
| 10,286,193 B2 | 5/2019 | Kamel et al. |
| 10,315,014 B2 | 6/2019 | Pigott |
| 10,470,905 B2 | 11/2019 | Yang et al. |
| 10,695,124 B2 | 6/2020 | Groff et al. |
| 10,729,454 B2 | 8/2020 | Root et al. |
| 10,758,717 B2 | 9/2020 | Gianotti et al. |
| 10,828,471 B2 | 11/2020 | Pigott |
| 10,864,354 B2 | 12/2020 | Adriaens et al. |
| 10,898,696 B2 | 1/2021 | Gianotti et al. |
| 11,154,693 B2 | 10/2021 | Pigott |
| 11,154,694 B2 | 10/2021 | Pigott |
| 11,202,892 B2 | 12/2021 | Pigott |
| 11,266,814 B2 | 3/2022 | Tanikawa et al. |
| 11,490,910 B2 | 11/2022 | Leuthardt et al. |
| 11,577,055 B2 | 2/2023 | Snow et al. |
| 11,602,362 B2 | 3/2023 | Nicholson et al. |
| 2002/0049408 A1 | 4/2002 | Van Moorlegem et al. |
| 2003/0009190 A1 | 1/2003 | Kletschka et al. |
| 2003/0050658 A1 | 3/2003 | Trask et al. |
| 2004/0049152 A1 | 3/2004 | Nayak |
| 2004/0215140 A1 | 10/2004 | Forman |
| 2006/0129093 A1 | 6/2006 | Jackson |
| 2006/0293612 A1 | 12/2006 | Jenson et al. |
| 2007/0005001 A1 | 1/2007 | Rowe et al. |
| 2007/0088380 A1 | 4/2007 | Hirszowicz et al. |
| 2007/0255305 A1 | 11/2007 | McMichael et al. |
| 2008/0167678 A1 | 7/2008 | Morsi |
| 2008/0183136 A1 | 7/2008 | Lenker et al. |
| 2008/0234795 A1 | 9/2008 | Snow et al. |
| 2008/0243067 A1 | 10/2008 | Rottenburg et al. |
| 2009/0125097 A1 | 5/2009 | Bruszewski et al. |
| 2009/0149807 A1* | 6/2009 | Bonnette ................. A61M 1/77 604/98.01 |
| 2009/0157006 A1 | 6/2009 | Nardeo et al. |
| 2009/0192537 A1 | 7/2009 | O'Brien |
| 2009/0234279 A1 | 9/2009 | Goldstein |
| 2009/0312786 A1 | 12/2009 | Trask et al. |
| 2010/0114017 A1 | 5/2010 | Lenker et al. |
| 2010/0262076 A1 | 10/2010 | Rowe et al. |
| 2010/0262124 A1 | 10/2010 | Hirszowicz et al. |
| 2011/0034949 A1* | 2/2011 | Solar ............... A61M 25/09016 606/194 |
| 2011/0040319 A1 | 2/2011 | Fulton, III |
| 2011/0112567 A1 | 5/2011 | Lenker et al. |
| 2011/0196410 A1 | 8/2011 | Besselink et al. |
| 2011/0218494 A1 | 9/2011 | Gerrans et al. |
| 2012/0029509 A1 | 2/2012 | Smith |
| 2012/0071856 A1 | 3/2012 | Goldfarb et al. |
| 2012/0101510 A1 | 4/2012 | Lenker et al. |
| 2012/0165680 A1 | 6/2012 | Akifumi |

(56) References Cited

U.S. PATENT DOCUMENTS

| | | | |
|---|---|---|---|
| 2012/0245520 A1 | 9/2012 | Kelly et al. | |
| 2013/0253467 A1 | 9/2013 | Gianotti et al. | |
| 2014/0107427 A1* | 4/2014 | Chow | A61M 25/1002 |
| | | | 600/249 |
| 2014/0171914 A1 | 6/2014 | Rowe et al. | |
| 2014/0243873 A1 | 8/2014 | Franklin | |
| 2014/0276530 A1 | 9/2014 | Gianotti | |
| 2014/0276585 A1 | 9/2014 | Gianotti | |
| 2015/0051632 A1 | 2/2015 | Sina | |
| 2015/0359549 A1 | 12/2015 | Lenker et al. | |
| 2020/0230376 A1 | 7/2020 | Pigott | |
| 2023/0166090 A1 | 6/2023 | Leung et al. | |

FOREIGN PATENT DOCUMENTS

| | | |
|---|---|---|
| CN | 202161434 U | 3/2012 |
| CN | 102451511 A | 5/2012 |
| CN | 202568333 U | 12/2012 |
| CN | 104470469 A | 3/2015 |
| CN | 106730247 A | 5/2017 |
| CN | 107847717 B | 10/2020 |
| CN | 107921244 B | 10/2020 |
| CN | 112057729 A | 12/2020 |
| CN | 109646053 B | 3/2022 |
| CN | 114533129 A | 5/2022 |
| CN | 111150933 B | 8/2022 |
| CR | 20160134 A | 8/2016 |
| EP | 0669143 B1 | 3/2003 |
| EP | 2616128 A1 | 7/2013 |
| EP | 2739335 B1 | 6/2015 |
| EP | 2968863 A2 | 1/2016 |
| EP | 2473122 B1 | 8/2016 |
| EP | 3082889 A1 | 10/2016 |
| EP | 2361103 B1 | 12/2016 |
| EP | 2292292 B1 | 4/2018 |
| EP | 2872209 B1 | 6/2018 |
| EP | 3322470 B1 | 11/2018 |
| EP | 3322471 B1 | 11/2018 |
| EP | 2421591 B1 | 12/2018 |
| EP | 3501589 A1 | 6/2019 |
| EP | 2768568 B1 | 5/2020 |
| EP | 4135625 A1 | 2/2023 |
| IT | MI20130816 A1 | 11/2014 |
| JP | 692888 B2 | 11/1994 |
| JP | 2001009038 A | 1/2001 |
| JP | 2005516742 A | 6/2005 |
| JP | 2007215864 A | 8/2007 |
| JP | 2012085816 A | 5/2012 |
| JP | 2012513294 A | 6/2012 |
| JP | 5619793 B2 | 11/2014 |
| JP | 5775082 B2 | 9/2015 |
| JP | 6743128 B2 | 8/2020 |
| KR | 20190020250 A | 2/2019 |
| KR | 102048413 B1 | 11/2019 |
| KR | 102201657 B1 | 1/2021 |
| KR | 102224259 B1 | 3/2021 |
| WO | 9416761 A1 | 8/1994 |
| WO | 1995008965 A1 | 4/1995 |
| WO | 9515782 A1 | 6/1995 |
| WO | 9920324 A1 | 4/1999 |
| WO | 0076424 A1 | 12/2000 |
| WO | 0249706 A2 | 6/2002 |
| WO | 2004008994 A1 | 1/2004 |
| WO | 2004028587 A2 | 4/2004 |
| WO | 2005076833 A2 | 8/2005 |
| WO | 2009005933 A1 | 1/2009 |
| WO | 2010075565 A2 | 7/2010 |
| WO | 2011139878 A1 | 11/2011 |
| WO | 2012037507 A1 | 3/2012 |
| WO | 2011027821 A1 | 2/2013 |
| WO | 2013177564 A1 | 11/2013 |
| WO | 2014151283 A1 | 9/2014 |
| WO | 2014188300 A1 | 11/2014 |
| WO | 2015065491 A1 | 5/2015 |

\* cited by examiner

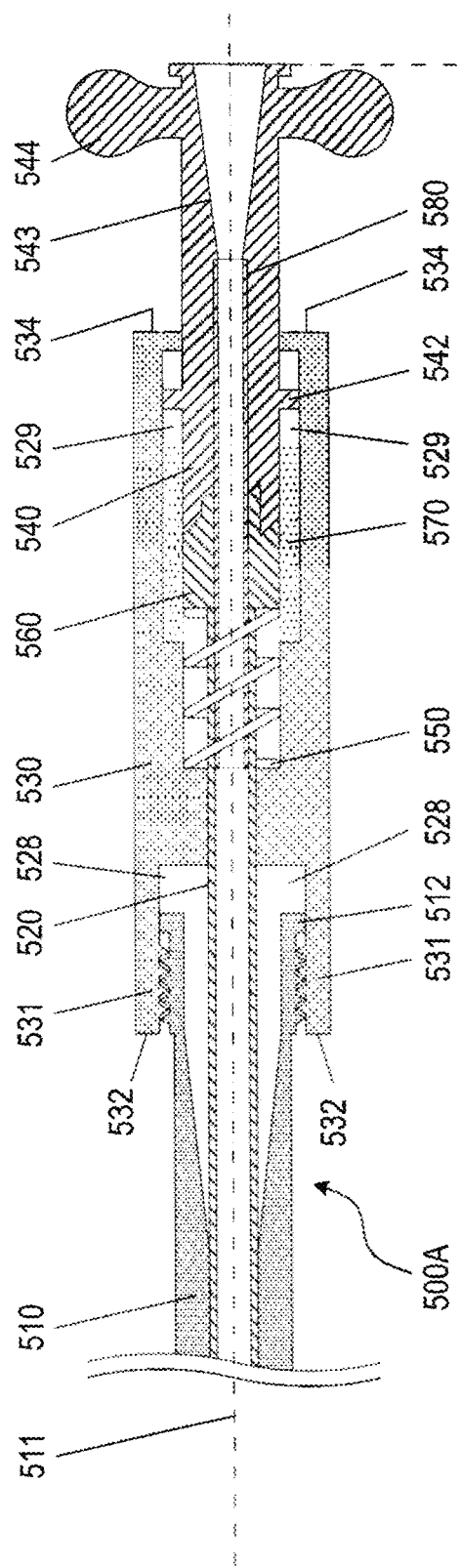
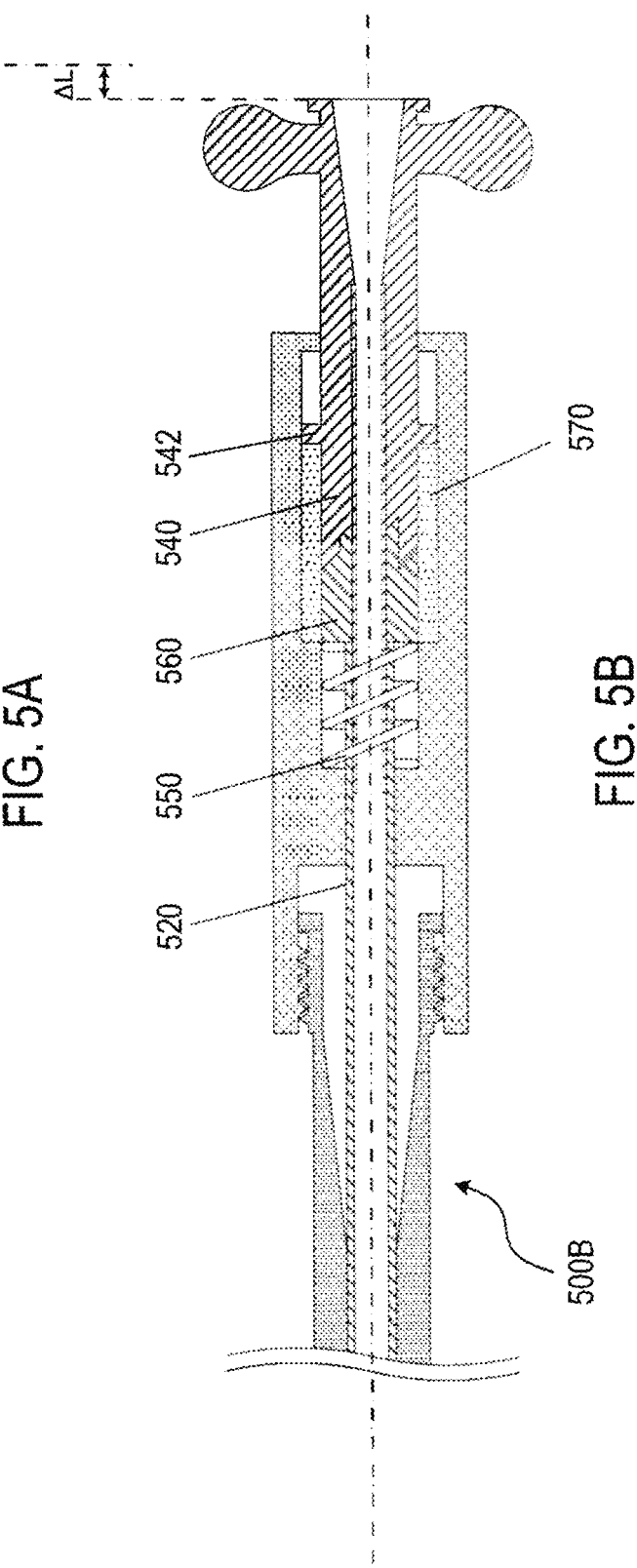
FIG. 5A
FIG. 5B

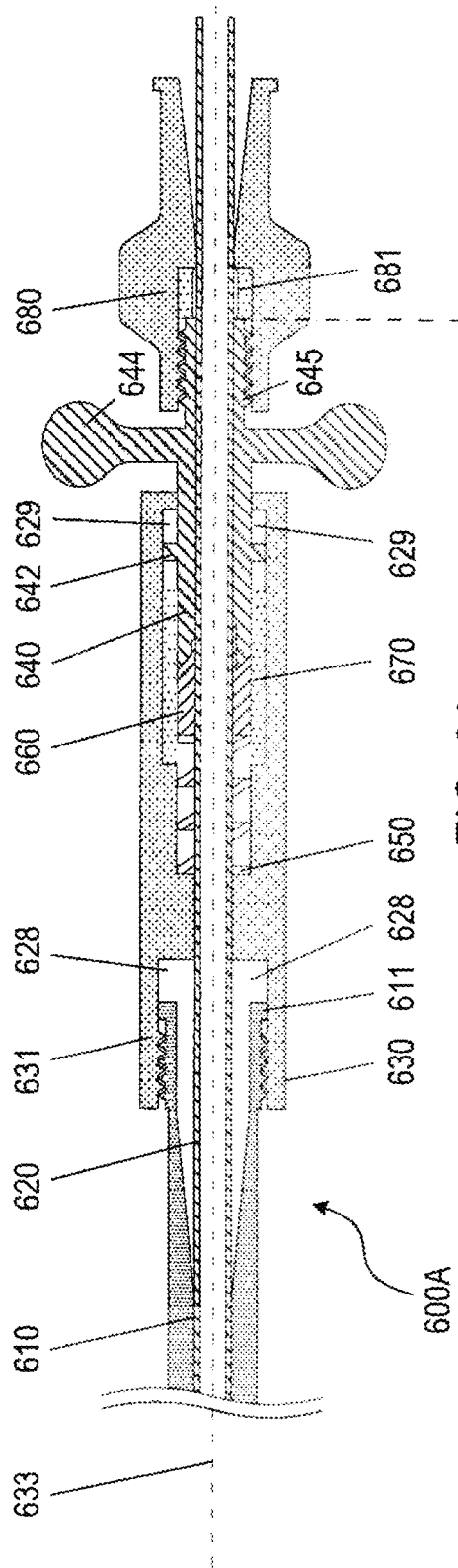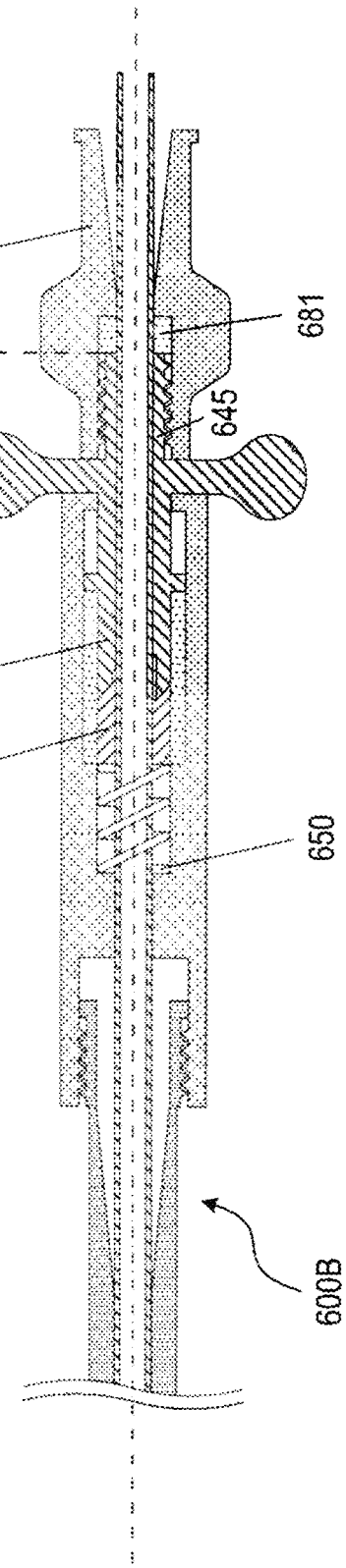
FIG. 6A
FIG. 6B

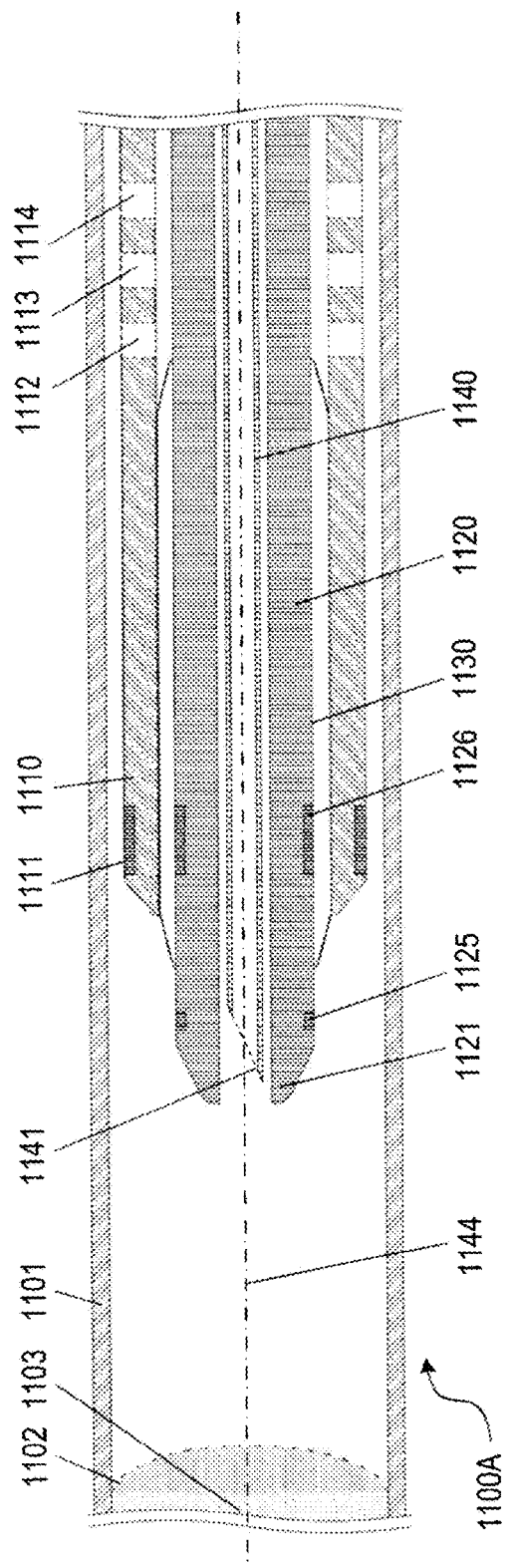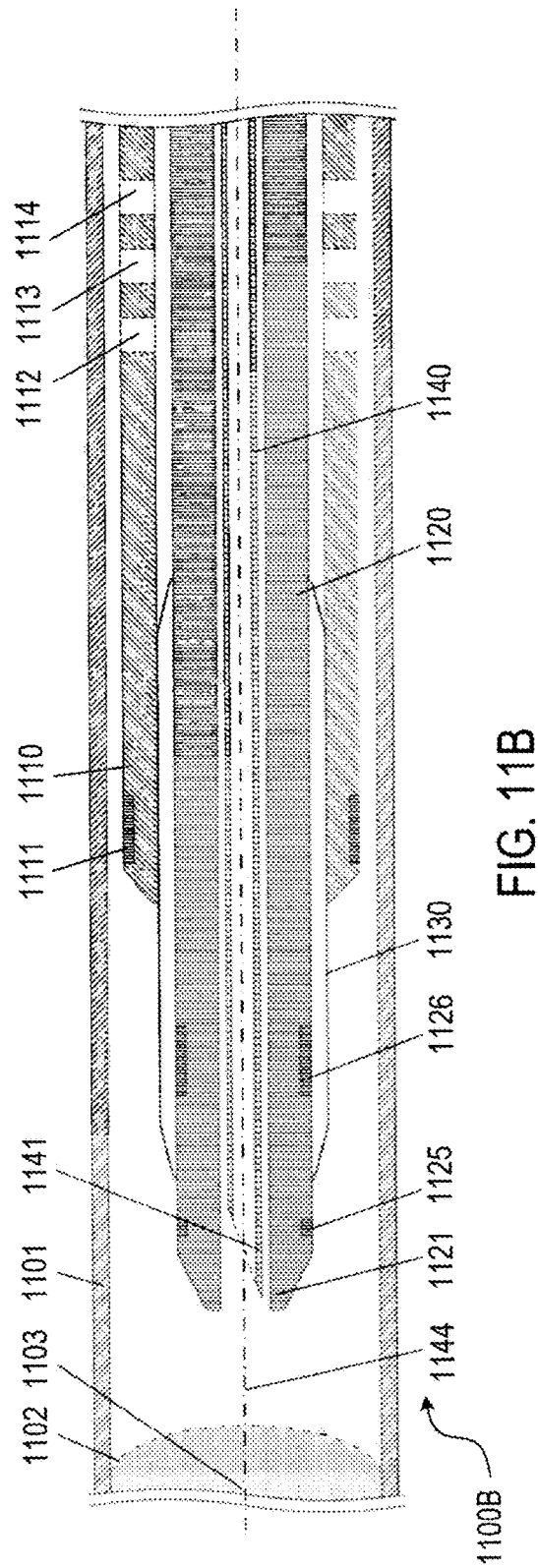

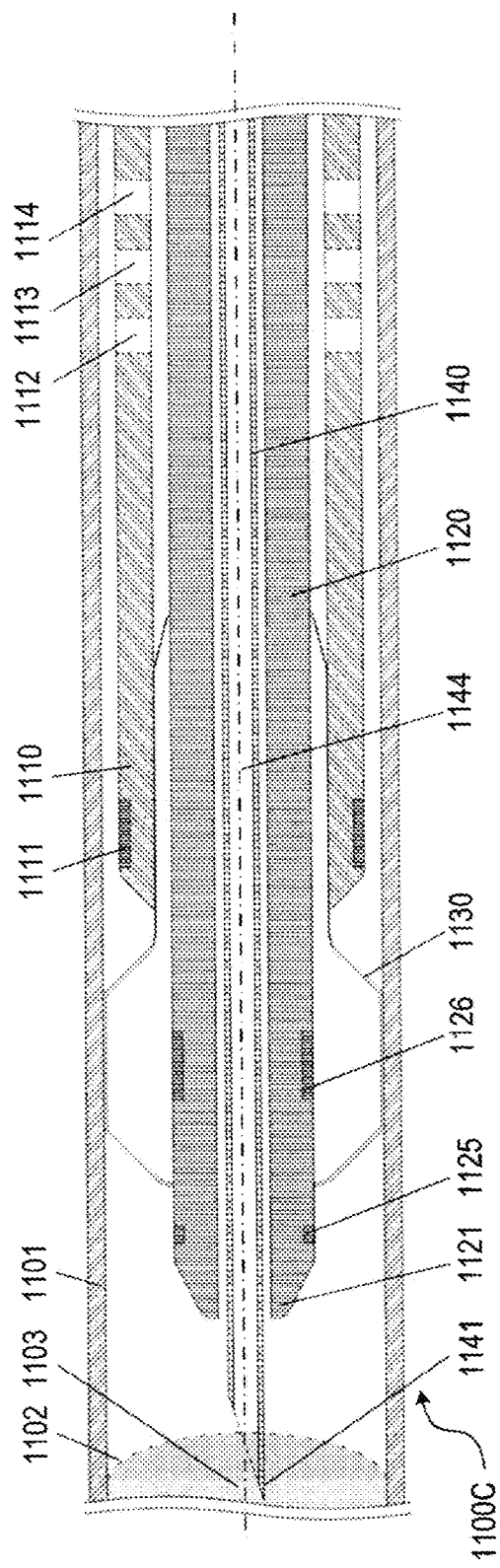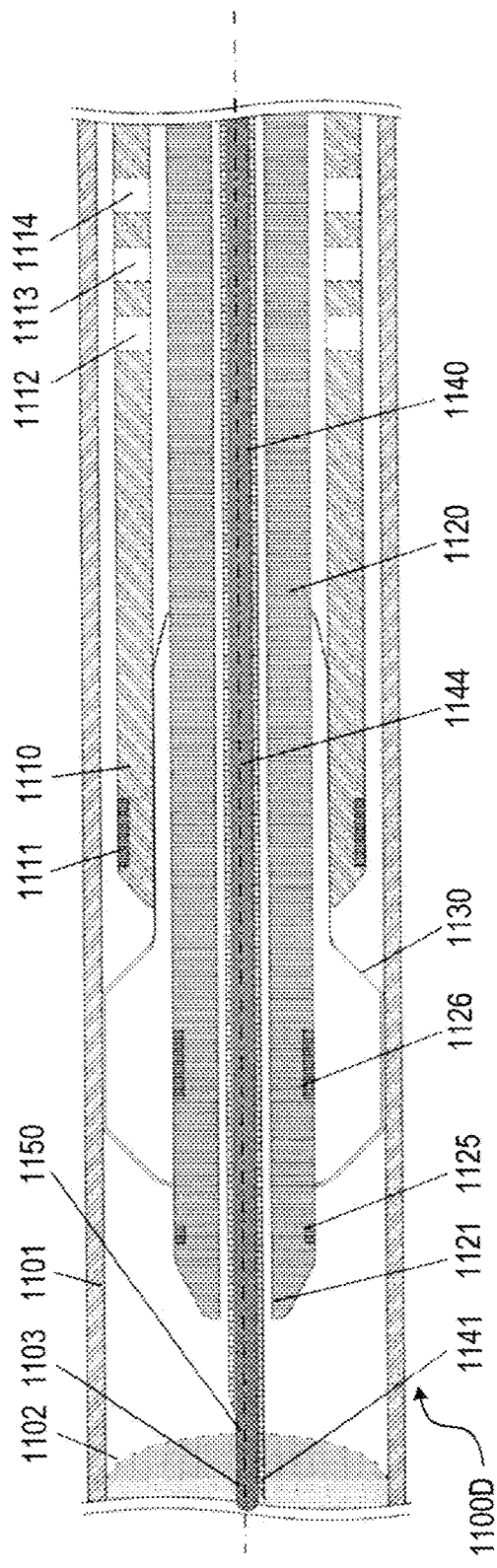

MECHANICALLY ACTUATED AND FUNCTIONALLY INTEGRATABLE CATHETER SYSTEM FOR TREATING VASCULAR AND NON-VASCULAR DISEASES AND RELATED METHODS

CROSS-REFERENCE TO RELATED APPLICATIONS

This application is a continuation-in-part of application Ser. No. 15/744,027, filed Jan. 11, 2018, which claims priority to PCT Application No. PCT/EP2016/050375, filed Jan. 11, 2016, which claims the benefit of U.S. provisional application 62/191,517, filed on Jul. 13, 2015, the content of which is hereby incorporated by reference in entirety.

TECHNICAL FIELD

The present disclosure is related to a mechanically enabled functionally integratable catheter system, comprising a support catheter, a dilator, a balloon catheter, and a lock-grip handle, which can be functionally and dimensionally configured by physicians for in vivo assembly to treat vascular and non-vascular conditions and diseases, including atherosclerotic lesions and chronic total occlusions.

BACKGROUND

Atherosclerosis is a vascular disease that involves accumulation of plaques, or lesions, within blood vessel walls that contain oxidized lipids, inflammatory cells, smooth muscle cells, and connective-tissue cells and that may additionally become calcified. Atherosclerosis is one of the major leading causes of death and morbidity in the Western world. Atherosclerosis can be asymptomatic at the early stages, without noticeable discomfort or pain. However, as the disease progresses, the lesions exhibit variable textures, become increasingly complex, and can cause successive reduction in lumen diameter; restriction of blood flow; and impairment of vessel flexibility as a result of substantial thickening and hardening of blood vessels. Accumulation of lesions can eventually restrict blood flow to a degree that the restricted blood flow is insufficient to support perfusion of tissues, leading to a condition known as "chronic total occlusion" ("CTO"). Recanalization treatments used to re-open obstructed vessels can present a number of technical challenges to engineers who design medical devices for recanalization and to physicians who depend on the use of the medical devices. Design engineers, medical-device manufacturers, and physicians continue to seek improved medical devices for treating atherosclerotic lesions and chronic total occlusions.

SUMMARY

The current document discloses a functionally integratable catheter system ("FICS") comprising functional units that can be assembled to produce different configurations. The functional units include: one or more FICS support catheters; one or more FICS dilators; one or more FICS PTA catheters; and one or more FICS lock-grip handles. Functional units can be provided in a pre-assembled form by the manufacturer, optionally pre-packaged as a device tray, for assembly into different configurations by clinical operators. The configurational adaptability of the FICS platform enables physicians to efficiently address multiple procedural aspects of treatment processes, including lesion access, lesion penetration, guide-wire negotiation, lesion recanalization, and dilation, by providing in situ treatment options, including intraluminal and/or extraluminal recanalization, and enables multi-stage, patient-customized treatments of complex lesions in vivo, including lesion-length-selective, multi-stage angioplasty treatment. FICS functional units can be, for example, selectively configured for recanalization of complex lesions by providing a length-adjustable balloon member that can be adjusted for treatment of target lesions having different lengths.

BRIEF DESCRIPTION OF THE DRAWINGS

FIGS. 5A-B illustrate cross-lateral views of a first dilator-tip propagation mechanism connected to the proximal end of an FICS support catheter.

FIGS. 6A-B illustrate cross-lateral views of a second dilator-tip propagation mechanism connected to the proximal end of the FICS support catheter.

FIGS. 11A-D illustrate cross-lateral views representing four consecutive configurational stages A-D for mechanically propagating a CTO penetration tip.

DETAILED DESCRIPTION

Figure 1:
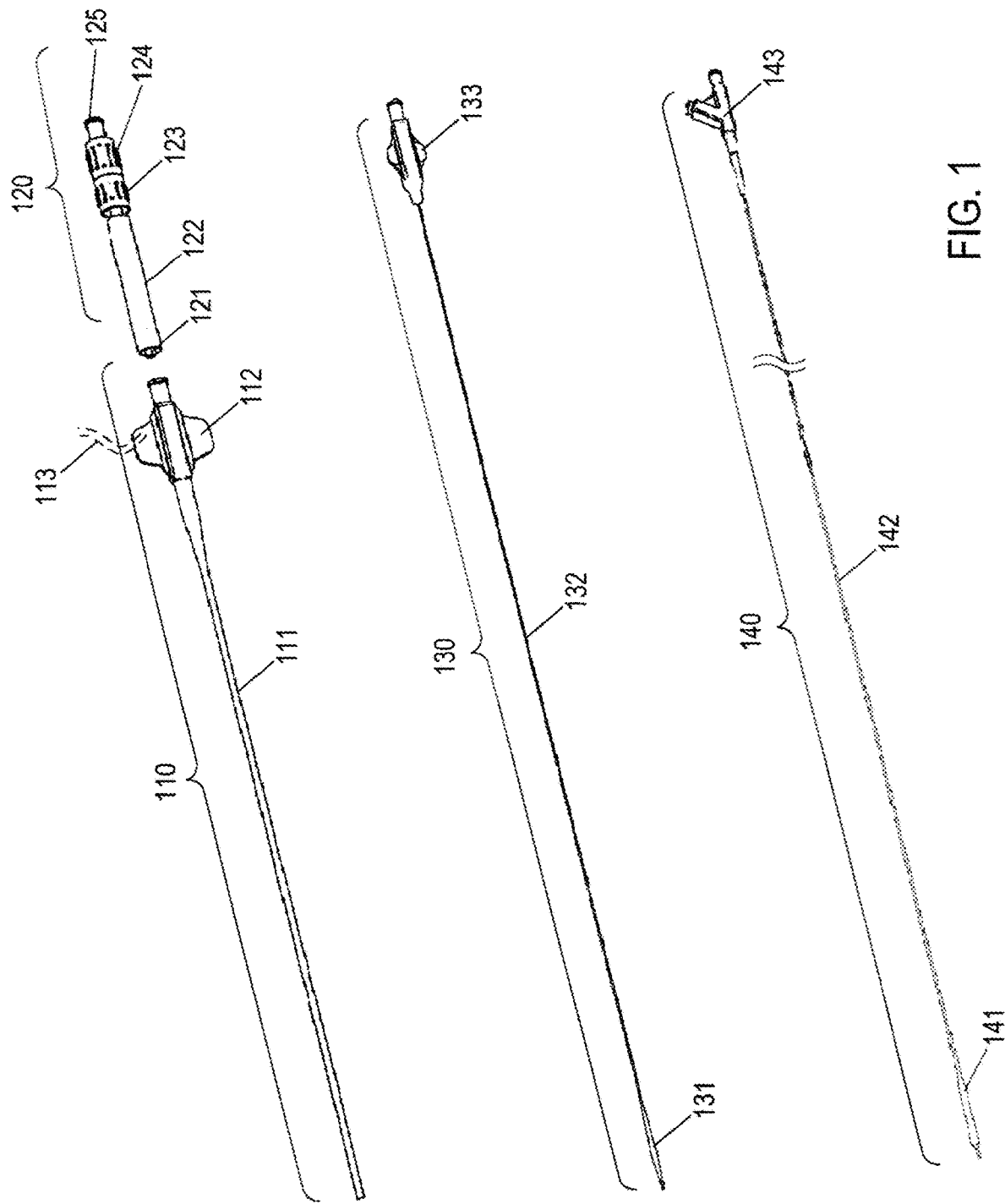
FIG. 1 illustrates the functional units of one implementation of the FICS in a pre-configured state.

A. Procedural Risks and Limitations of Current Medical Devices and Procedures for Treating CTO and Complex Atherosclerotic Occlusions/Lesions Atherosclerosis can be generally classified into coronary, neurovascular or peripheral vascular disease subtypes, involving the progressive deterioration of cerebral, carotid, coronary, renal, hepatic, aortoilliac, iliac, gonadal, femoral, popliteal, and below-the-knee (BTK) arteries and veins. The diseased body can compensate for the gradual impairment of vascular functions by forming alternative collateral vessels in order to maintain adequate blood supply to dependent tissues and organs. However, such compensation mechanisms are only temporarily effective, and are marginally adequate for sustainably perfusing dependent tissues/organs. Insufficient perfusion of critical organs can have devastating effects, often resulting in one or more increasingly severe complications that can be triggered/exacerbated by atherosclerotic vessels, including: angina pectoris, myocardial infarction ("MI") and congenital heart failure, often leading to patient mortality. Patients suffering from a peripheral vascular disease, resulting from the blockage of one or more peripheral blood vessels, are highly likely to experience the onset of multiple related complications (in the order of disease severity): claudication, ischemic rest pain, ulcerations, critical limb ischemia ("CL"), gangrene, and/or tissue necrosis. In addition to raising the risks for requiring surgical interventional procedures, including bypass placement and limb amputations, some acutely life-threatening complications caused by vascular diseases may increase the risks for developing embolisms and strokes.

Lack of adequate perfusion through narrowed, stenotic, or occluded blood vessels can be treatable by various interventional procedures that can be suitably selected for patient-specific situations, taking into consideration several clinically relevant factors. In general, effective therapeutic interventions may involve systemic administration of one or more suitable pharmaceutical agent(s) in conjunction with minimally invasive, locally administered interventional procedures requiring the application of one or more atherectomy devices, balloon dilation catheters, and/or stents by a practicing clinician. For example, a balloon dilation catheter can be utilized for treating coronary vessels during percutaneous transluminal coronary angioplasty ("PTCA") and during a percutaneous transluminal angioplasty ("PTA"). However, if lesions, malformations, constrictions, obstructions and blockages within arteries/veins are not effectively treatable by standard vascular interventional therapy, then surgical intervention may be necessary, including open surgery that can be effective for surgically forming a bypass composed of an autograft vein removed from a patient, or a synthetic graft, around the diseased vessel segment. However, if tissue damage is deemed irreversible and beyond salvage, then bypass or surgical amputation of the affected limb may be the only option. Generally, surgical treatments can pose substantial risk and trauma for many symptomatic patients. Even if the outcome is deemed successful, the surgery may leave a profound and permanently debilitating impact on patients' mobility, life expectancy, and overall quality of life.

As an effective and less risky alternative to drastic surgical procedures, interventional procedures have become more widely accepted and modestly practiced, if warranted by patient-specific circumstances. To propose treatment strategies and recommendations for the management of peripheral arterial disease, the European Society of Vascular Surgery and the World Federation of Vascular Surgery Societies have published the Trans-Atlantic Inter-Society Consensus document (TASC; 2000. TASC II: 2007). These recommendations provide general guidance for treating various types of lesions depending on their dimensions (length, diameter), degree of occlusion, and type of affected vessels. According to TASC, least severe TASC A lesions have been deemed most suitable for endovascular procedures, while surgery has been primarily recommended for most severe TASC D lesions. "TASC D" lesions refers to chronic total occlusion of the common or superficial femoral artery and to chronic total occlusion of the popliteal artery and proximal trifurcation vessels. However, endovascular therapy for complex lesions of the superficial femoral artery and popliteal artery remains controversial. TASC acknowledges that more clinical evidence may be required to base firm recommendations for treating TASC B and C lesions by PTA procedures. Type B lesions include conditions involving multiple lesions (55 cm) (e.g., stenoses or occlusions); single stenosis or occlusion (515 cm) not involving the infrageniculate popliteal artery; single or multiple lesions in the absence of continuous tibial vessels to improve inflow for a distal bypass; heavily calcified occlusion (s5 cm); and single popliteal stenosis. Type C lesions include conditions involving multiple stenoses or occlusions (>15 cm) with or without heavy calcification, and recurrent stenoses or occlusions that have been previously treated by two endovascular interventions.

In particular, chronic occlusions represent a significant portion of vascular pathologies and have historically presented a serious technical challenge for interventional practitioners that rely on conventional guide wires and catheters for accessing plaques/lesions. The treatment outcomes depend on the morphological and compositional characteristics of a given chronic total occlusion, in that softer and less compacted CTO plugs can be relatively easier to displace as compared to densely calcified CTO caps that may be impenetrable in the most challenging situations. Thus, chronic total occlusions, which may be considered as a separate clinical pathology most commonly encountered in TASC D lesions, can remain procedurally challenging when treated by percutaneous transluminal angioplasty, contributing significantly to procedural failure rates for peripheral interventions. Despite the various technical challenges associated with CTO treatments, such minimally invasive interventional vascular approaches have been increasingly preferred as the first option for treating peripheral disease conditions to avoid substantial risk of mortality associated with conventional bypass surgery. Unfortunately, the success rates for intraluminal and subintimal CTO recanalization techniques as conventionally practiced using conventional guide wires and catheter devices remain only moderate at best. There is a persistent need to provide various patient-adaptable interventional devices that can be customized by physicians for more effective treatment of vascular conditions/diseases, such as associated complex lesions and CTOs.

As a first procedural step, percutaneous guidewire negotiation by intraluminal intervention can be attempted to cross and recanaize chronic occlusions. However, the application of standard guide wires and catheter devices to enable percutaneous intraluminal recanalization of CTOs have shown only moderate procedural success. Failure in guide wire negotiations can lead to failure in CTO recanalization. Factors that may significantly impact the prospective outcome include: lesion length, patient-specific anatomical tortuosity, lesion-cap calcification, medical operator skill and presence of run-off vessels. In more recent years, subintimal recanalization with distal reentry, known as percutaneous intentional extraluminal recanalization ("PIER"), has been increasingly advocated as a viable alternative approach when intraluminal passage remains procedurally unsuccessful. This technique has been applied with considerable technical success for superficial femoral artery ("SFA") angioplasty, where multi-segmental, extended, calcified occlusions exhibiting mean occlusion lengths of 215 cm can be regularly observed.

Subintimal CTO recanalization approaches have been somewhat successful, although the technique itself may not be applicable in all cases. Typically, subintimal CTO recanalizations require most advanced levels of physician experience, skills, and general expertise because controlling the reentry into the true lumen of a target vessel and finding positional control of the reentry site can be potentially problematic for the inexperienced and/or unskilled. For example, vessel trauma and uncertain complications may result if reentry site is extended significantly and distally from the targeted vessel lumen region, thereby increasing the likelihood for subsequent subintimal angioplasty, or stenting to be required beyond the occluded vessel section. In the worst-case scenario, improper guide wire negotiation for CTO recanalization can cause vessel trauma, rupture, dissection and/or bleeding due to inadvertent vessel wall perforation. A certain level of flexibility is desirable for guide wire tip sections and distal shaft portions, which enables efficient, atraumatic vessel navigation. When attempting CTO penetrations, however, this flexibility can cause the guide wire tip and shaft sections to buckle or kink, and can negatively impact the overall positional controllability of the guide wire, affecting device stability during implementation. The guide wire tip may be deflected from the typically hardened cap surface region of the CTO, causing the tip to veer eccentrically away from densely calcified plaque tissue into adjacent soft vessel walls. Once a subintimal passage has been inadvertently formed, the subsequent application of adjunct therapeutic devices, such as atherectomy catheters or balloon dilation catheters, can be substantially impeded or procedurally prohibited. Furthermore, the guide-wire penetration capability can be directly proportional to the shaft stiffness, which can be inversely proportional to having navigational flexibility, and therefore, the relatively flexible guide wire may require some additional form of guiding support to provide a safe yet effective measure of pushability.

As is the case for most medical devices, the various interventional devices and procedures for treating vessel occlusions have not satisfied all procedural challenges encountered during practical applications. Most interventional physicians must rely on device manufactures to provide all necessary equipment and implements in treating a broad spectrum of lesions/occlusions exhibiting different lengths, density, and severity. This limitation becomes acute especially for the treatment of complex lesions and total occlusions, where it is common for physicians to improvise by recombining various approved medical-device components to devise make-shift combinations for those situations where a single pre-made device can be insufficient and alternatives are non-existent. Many medical devices and implements can serve multiple general functions and may not be designed for a specialized end use and/or devices made by different manufactures may not be functionally compatible to work together due to different material properties and/or dimensional configurations. Under the current circumstances, significant expertise and skill can be required to recanalize multiple numbers of chronic total occlusions. Significant physician judgement can guide procedural decisions as to the optimal combination of different medical device components to affect a desired therapeutic outcome. Technical challenges can include the selection and dimensional matching of various medical device components that can work well together during multi-staged, complex procedures.

B. Functionally Integratable Catheter System" ("FICS") for Treating Complex Atherosclerotic Lesions/Occlusions The present disclosure provides a comprehensive multifunctional device platform that provides for different instrument configurations directed to patient-specific anatomies and useful for treating complex and total occlusions. This device platform enables physicians to effectively treat the most challenging and complex lesions/occlusions more conveniently and in less time. The current document discloses provides a Functionally Integratable Catheter System ("FICS") comprising functional units and subunits that can be configured to assemble a variety of different instruments. The FICS includes: one or more FICS support catheters: one or more FICS dilators; one or more FICS PTA catheters; and one or more FICS lock-grip handles. Each functional unit can be provided in a pre-assembled form by the manufacturer, and optionally co-packaged as a device tray that includes the functional units. Examples of therapeutic-specific functional subunits include various CTO penetration tips and reentry tips. Tips can be designed specifically for treating a particular type of complex lesion and/or CTO. FICS configurations that include a FICS dilator incorporating a CTO penetration tip can be utilized during intraluminal recanalization. FICS configurations that include a FICS dilator incorporating a reentry tip can be utilized during extraluminal recanalization. Although individual functional units may be operational in a pre-configured state, a functional unit may have limited functionality as a standalone device.

Many patients suffering from advanced atherosclerosis demonstrate multiple complex lesions along a common affected vessel, meaning that therapeutic intervention requires the sequential treatment (access, recanalization, and dilation) of all plaques/lesions in order to restore patency to sufficient levels. FICS provides a set of inter-operable functional units conceptually analogous to a broad range of situation-specific implements that can be co-assembled by physicians. After employing a first hypothetical FICS configuration in a first interventional procedure, such as treatment of a first occlusion, FICS functional units can be reassembled into a different configuration for a second subsequent interventional procedure, such as treatment of a second occlusion. FICS configurations can be repeatedly disassembled and reassembled by clinical operators performing simultaneous and/or sequential applications in vivo. Because of the interoperability of FICS functional units with respect to a pre-deployed guidewire, the FICS support catheter and guide wire can remain in situ, without being retracted for repositioning, in order to treat a second or subsequent lesion present in a vessel undergoing treatment, access to multiple lesions can be continuously maintained, procedural steps can be reduced to save time and money, the quality of the procedure can be increased, and the operational convenience to practitioners is significantly improved.

C. Co-Assembling the Functional Units of the FICS

In the following subsections, the FICS functional units are described in further detail and illustrated in FIGS. 1-15. Dimensional characteristics are described in the Examples and Tables 1-7. For convenience, FIG. 15 illustrates, in a flow-chart overview, possible FICS configurations and provides a visual map of the various functional units and functional subunits that can be selectively combined by a clinical operator for constructing therapeutic-specific configurations for treating a broad range of complex lesions and CTOs.

1. Operational Configurations of the FICS 1.1 the Pre-Configured Functional Units of the FICS FIG. 1 illustrates the functional units of one implementation of the FICS in a pre-configured state. FIG. 1 shows four separable functional units: (1) a support catheter 110; (2) a lock-grip handle 120; (3) a dilator 130; and (4) a PTA catheter 140. These separable functional units can be assembled to produce different configurations that serve various therapeutic purposes. The support catheter, the dilator, and the PTA catheter are dimensionally adaptable for interoperability. In one implementation, the variable total length ("VTL") of configurations ranges from approximately 90 to 220 cm. In this implementation, the variable usable length ("VUL ranges from approximately 60 to 180 cm.

In FIG. 1, the FICS support catheter 110 comprises a shaft member 111, one or more flushing ports 113, and a manifold member 112 with a female luer lock adapter, which can be connected to the FICS lock-grip handle 120 comprising a male luer adapter 121, an external casing member 122, a hemostatic valve portion 123/124, and a female luer adapter 125. The support catheter further comprises a central lumen into which an FICS dilator or FICS PTA catheter is inserted. In the illustrated implementation, the distal edge of the FICS support catheter is straight-edged, unlike conventional support catheters having tapered distal edges. The straight edge of the FICS support catheter is a design feature that improves the interoperability between the FICS support catheter and FICS dilators and FICS PTA catheters and is functionally augmented by insertion of additional functional units to form a seamless, atraumatic edge (e.g., FIG. 12A). The straight distal edge may include a reinforced tip region comprising or including a radiopaque material. The FICS support catheter shaft and tip region can be formed from a flexible polymer. The polymer may contain braided mesh embedded as a structural reinforcement. The reinforced shaft and reinforced tip region can be designed to withstand positive and negative pressures exerted on the system, including both nominal balloon-inflation pressure ranges and pressures that exceed burst pressure. At substantially the same time, the reinforced shaft can physically constrain the radial expansion of an inflatable member sheathed or contained by the reinforced shaft. Furthermore, such semi-rigid material compositions/combinations can provide for improved device pushability, directional bending capability, and mechanical support for enhancing vessel guidance. The FICS support catheter may include, in certain implementations, one or more flushing orifices that can be incorporated on the proximal lateral surface of the distal edge for delivering and aspirating contrast fluid and saline solutions utilized during interventional procedures. These orifices can be fluidly connected to the central lumen of the support catheter. The fluids can be introduced into, or removed from, the lumen, in the presence or absence of other insertable functional units, via one or more flushing ports (113) integrated into the FICS support catheter manifold. The flushing port can be integrated into the manifold as a separate luer inlet, or alternatively, the manifold may include a two-way valve attached to the flushing port to enable media transport and to enable aspiration, perfusion, and suction functionalities. The manifold may further comprise an additional balloon introducer and/or a hemostatic seal with an optional locking mechanism operationally coupled to the manifold to temporarily stabilize interconnection of multiple FICS functional units. An FICS support catheter can include one or more distally positioned radiopaque markers placed along the shaft surface (e.g., proximal to the distal tip) to enable angiographic device visibility, such as for tracking the tip position within blood vessels. An FICS support catheter, in certain implementations, includes one or more visual or haptic surface markings for aiding the assembly of FICS functional units and for positional guidance, such as indicating, to a user, the locations of flushing holes. An FICS support catheter can be used as an introducer sheath in certain cases; for example, when performing an interventional procedure via radial or brachial access. Use of an FICS support catheter as an introducer sheath effectively reduces the number of components required for certain procedures. Certain implementations of the FICS support catheter can function as aspiration catheters in the absence or presence of other FICS functional units.

In FIG. 1, the FICS lock-grip handle 120 can function as a user handle for physician operators. The FICS lock-grip handle 120 can provide relative positional stabilization, position fixation, length adjustment, and hemostatic sealing for the interconnecting functional units, improving the general handling of the system. The FICS lock-grip handle comprises a spring-loading mechanism for dilator-tip propagation. The FICS lock-grip handle can be designed as a simple polymeric cylinder, clip, wedge, or screw that can be reversibly attached to an FICS support catheter an FICS dilator, and an FICS PTA catheter. Certain implementations of the FICS lock-grip handle can be attached at the proximal, non-indwelling shaft portion of the FICS support catheter. Operational coupling of the FICS lock-grip handle to the other FICS functional units can provide relative positional stabilization, including longitudinal distance adjustment between the units. The internal hemostatic seal of the FICS lock-grip handle can be designed to accommodate functional units of varying diameter. The FICS lock-grip handle can include visual, acoustic, or haptic markings for improved length adjustability and handling by clinical operators. In certain implementations, the FICS lock-grip handle can be configured to simultaneously attach to an FICS support catheter and to an FICS dilator, facilitating partial exposure of an FICS-dilator. In certain implementations, the FICS lock-grip handle can be firmly attached to an FICS support catheter by thermal or adhesive bonding, welding, gluing, screwing, snapping, clipping, interference fit, insertion, and/or coaxial alignment. In certain implementations, an FICS lock-grip handle can coaxially receive an FICS dilator by mechanically adhering, snapping, sliding, screwing, clipping, wedging, or keying into the dilator shaft. In certain implementations, an FICS lock-grip handle can include a hub, an adaptor, a connector element, a fitting, a jack, or a socket complementary to an interlocking or mating surface element of components with which the FICS lock-grip handle is joined. In certain implementations, an FICS lock-grip handle provides a mechanical end stop, limiting the longitudinal displacement of either an FICS dilator shaft, an FICS dilator tip, and/or an FICS PTA proximal balloon cone.

In FIG. 1, the FICS dilator 130 comprises a dilator tip 131, a shaft member 132, and a manifold member 133. In certain implementations, an FICS dilator can incorporate additional structural features to provide multiple functionalities. In certain implementations, an FICS dilator may include: (1) a distally positioned, non-anchoring (non-inflatable) dilator tip segment having a single guide-wire lumen; (2) a distally positioned, anchoring and centering (inflatable) dilator tip segment with a dual lumen, including a lumen guide-wire lumen and an inflation lumen that can be fluidly connected to the inflatable member: and (3) an inner tubular member, coaxially embedded within a distal dilator tip segment, serving as a mechanically actuatable component that is extensible along a portion of the distal dilator tip and that can be sheathed/concealed within the dilator tip during transport. The inner tubular member may be a hollow-bore hypotube, further including a tip (lancet). In certain implementations, an FICS dilator can contain a substantially rigid tip region or segment, capable of occlusion penetration, which can be embedded or partially encapsulated within a tapered, substantially soft polymeric material to facilitate atraumatic vessel guidance and effective occlusion penetration. In certain implementations, the rigid tip can be manufactured from a tubular member, such as a hypotube. In other implementations, the tip and selected shaft regions of an FICS dilator comprise elements and/or structures of dissimilar mechanical properties to facilitate variable stiffness in certain sections of the dilator shaft. In certain implementations, the tapered dilation tip can form a seamless and atraumatic transition to the support catheter shaft or mantle. The distal shaft section of the FICS dilator may include one or more inflatable members that center and safely anchor a dilator in a target vessel region. In certain implementations, one or more distally positioned, radiopaque markers can be placed on the dilator shaft surface to enable angiographic device visibility for precise positional verification. The hypotube tip shape and construction may be modified to serve as an inflexible/non-malleable CTO penetration tip or a flexible/malleable reentry tip. A FICS dilator shaft may be composed of an incompressible shaft material, such as a metal or a rigid polymer, and may be additionally reinforced.

In FIG. 1, the FICS PTA catheter 140 comprises an inflatable member 141, generally a balloon, a catheter shaft 142, and a manifold member 143. The FICS PTA catheter can incorporate standard features found in conventional PTA catheter products. However, in contrast to other PTA catheters, the FICS PTA catheter includes an inflatable member portion of constant length that can be concentrically concealed within an outer sheath formed by the FICS support catheter. During operation, the balloon member of the PTA can be advanced from the distal portion of the support catheter, controllably exposing an inflatable portion of the balloon member to a desired length capable of effectively dilating the length of a target lesion situated along an affected vessel in need of treatment. The length of the inflated portion of the balloon can be adjusted according to the length of the target lesion so that lesions of various lengths can be effectively dilated/treated. Multiple radiopaque markings can be provided at the distal end of the support catheter shaft and/or at the distal end of the balloon to provide visual guidance for determining the length for the balloon exposed from the support catheter. The VUL of the PTA catheter correlates with the VUL of the inflatable member by enabling a clinical operator to control the length of the balloon that can be exposed from the support catheter during an in vivo lesion-length-selective balloon-dilatation process. First, an FICS PTA catheter can be inserted into an FICS support catheter and stabilized utilizing the lock-grip handle to form an in situ length-selective FICS PTA configuration capable of treating lesions of variable lengths utilizing a single balloon member that can be inflated at variable lengths. An FICS PTA catheter and the inflatable member portion can be reversibly removed from the FICS support catheter during operation. The length of the support catheter can be dimensionally configured so that a portion of the balloon is maintained in an uninflated state by retaining the portion of the balloon within the distal end of the support catheter during inflation and deflation of the remaining portion of the balloon. By this method, the original balloon-folding capability of the sheathed portion of the balloon is maintained to facilitate multistage PTA treatments and to preserve an optimal shape of the inflatable portion of the balloon. The FICS PTA catheter shaft can be composed of a substantially incompressible material, for example a hypotube formed from metal or a rigid polymer, which may be reinforced.

1.2 FICS Operational Configurations/Assembly of FICS Functional Units

The separable functional units of the FICS can be assembled and reassembled into different functional configurations, by physician operators, for selective adjustment to meet the needs of phase of a multi-staged angioplasty procedure. The FICS configurations can be variably customized by a practicing physician to address different challenging situations encountered in treating patients who are seriously affected with advanced stages of arteriosclerosis, including patients having multiple lesions, lesions with extended lesion lengths, complex anatomies, and total occlusions. For clinical situations involving chronic total occlusions, target obstructions may be either intraluminally penetrated, by passing an instrument through the CTO cap directly, or extraluminally circumnavigated, by passing an instrument through the subintimal vessel wall, before crossing and dilating the affected lesion/occlusion. The presence of multiple lesions requires sequential treatment for each lesion/occlusion having certain length/texture characteristics. An ideal therapeutic instrument would be amenable to in vivo adjustment by a user for therapeutic-specific applications. The multi-configurational operation of the FICS functional units provides a number of advantages: (a) procedural/clinical effectiveness in treating multiple and complex lesions/CTO's; (b) substantial operational freedom/flexibility due to interoperable functional units enabled for reversible assembly; (c) substantial operational convenience for physicians; (d) substantial time savings for the benefit of both patients and physicians; and (e) quality PTA with comparably less dissections. FICS functional units can save procedural clinical time by enabling convenient interchangeability between different functional units so that physicians can quickly adapt the FICS functional units for each procedural phase, which may vary in procedural complexity depending on the characteristics of a plaque/lesion without the necessity for withdrawing the support catheter for treatment of each successive plaque/lesion during a sequential procedure. For example, after employing a first FICS configuration in a first interventional procedure during a treatment procedure carried out on a patient with multiple lesions or occlusions. FICS functional units can be assembled and/or reassembled into a different configuration for a second interventional procedure. Disassembly and reassembly may be repeated multiple times, as necessary, by clinical operators performing simultaneous and/or sequential applications in vivo. The interoperability of FICS functional units involving a pre-deployed FICS support catheter allows the FICS support catheter to remain deployed near the treatment site for enabling continuous lesion access throughout the treatment of an affected vessel and rapid exchange of additional FICS functional units that may be insertable through the FICS support catheter lumen for treating a second or subsequent lesion present in the same affected vessel. By eliminating a need for retracting the FICS support catheter for repositioning, time is saved and operational convenience is provided.

Figure 2:
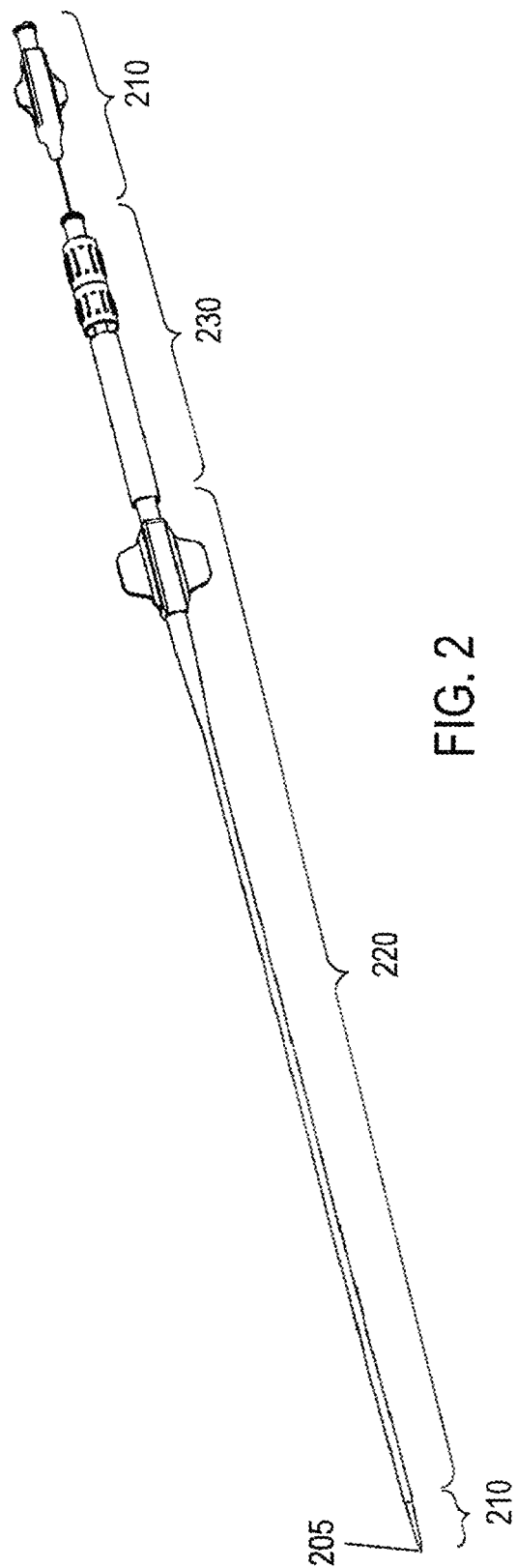
FIG. 2 illustrates an assembled "FICS dilator configuration" adaptable for intraluminal and/or extraluminal recanalization.

FIG. 2 illustrates an assembled "FICS dilator configuration" adaptable for intraluminal and/or extraluminal recanalization. An FICS dilator can be combined with an FICS support catheter to produce an FICS CTO-dilator configuration, adapted with a suitable CTO penetration tip 205 for intraluminal recanalization. In FIG. 2, an FICS CTO-dilator configuration can be assembled by attaching an FICS lock-grip handle 230 to the FICS support catheter 220 and coaxially inserting an FICS dilator 210 through the assembled FICS support catheter/lock-grip handle so that the CTO-penetration dilator tip 205 at the distal end of the FICS dilator can be positioned and locked to partially exit from the distal end of the FICS support catheter tubing, as shown. When assembled with the FICS CTO dilator, the FICS support catheter facilitates CTO penetration in a pressure-controlled and displacement-controlled manner.

The FICS dilator can be combined with the FICS support catheter to form the FICS "Reentry Dilator configuration," adapted with a suitable "Reentry Tip" 205 in FIG. 2 for extraluminal recanalization. FIG. 8B provides a more detailed description of the "Reentry Tip" shown as 205 in FIG. 2. FIGS. 7 A-D provide a detailed description on alternate projectable dilator tip designs having additional functionalities. FIGS. 12 A-B illustrate the operational mechanism for the mechanically actuated tips.

As shown in FIG. 2, an FICS-reentry-dilator configuration is assembled by attaching the FICS lock-grip handle 230 to the FICS support catheter 220 and coaxially inserting the FICS dilator 210 through the assembled support catheter/lock-grip handle so that the reentry tip 205 can be positioned and locked to partially exit from the distal end of the FICS support catheter tubing, as shown. The dilator tip 205 is attachable to the dilator hub 210 via a tubular, elongated member (FIG. 1, item 132). The dilator hub can be designed to be manually rotatable, enabling directional orientation of the conjoined tip portion. When co-assembled with an FICS lock-grip and an FICS support catheter, the FICS dilator can facilitate CTO circumnavigation, subintimal access, and reentry in a controlled manner with respect to directional orientation, pressure, and displacement. The reentry tip may be provided for simultaneous use with a designated CTO guide wire, in which the guide wire serves a CTO penetration function, and the reentry tip in conjunction with the FICS dilator hub provides a steering function for the guidewire. As an alternate embodiment, the reentry tip in conjunction with the FICS dilator hub can provide a steering function for the guidewire in facilitating convenient side branch vessel access.

Figure 3:
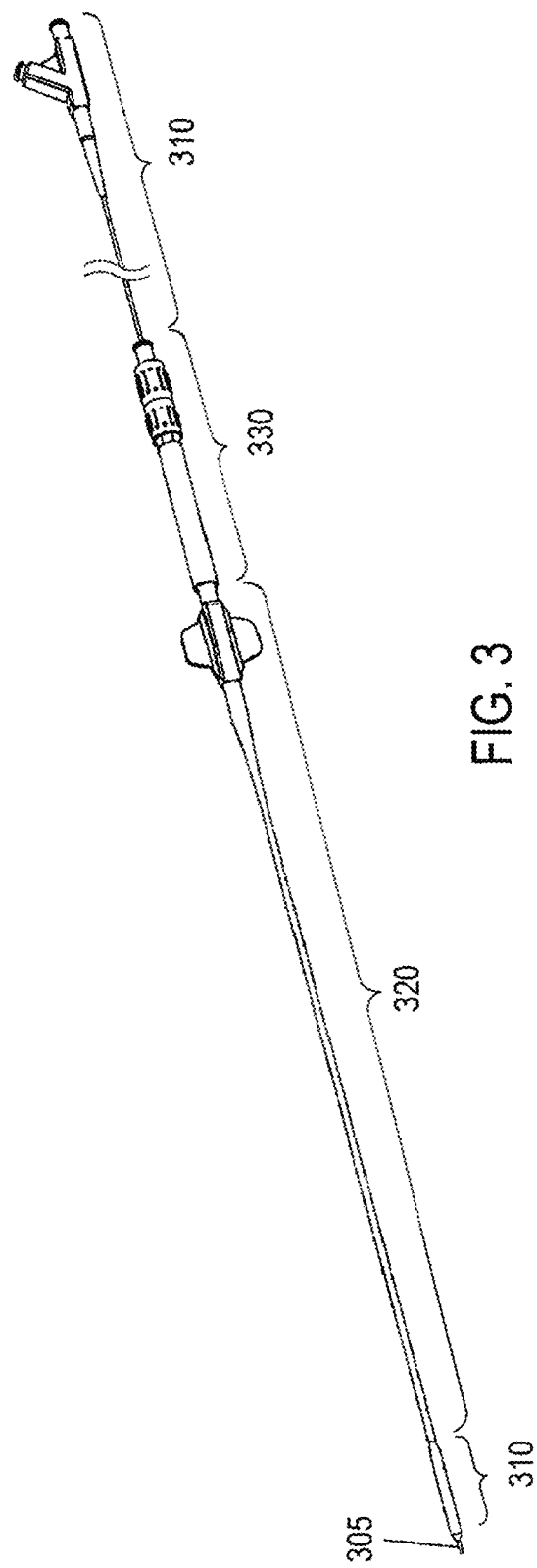
FIG. 3 illustrates an FICS LLS PTA catheter configuration useful for lesion-length selectivity.

FIG. 3 illustrates an FICS LLS PTA catheter configuration useful for lesion-length selectivity. As shown in FIG. 3, an FICS LLS PTA catheter configuration is assembled by attaching a lock-grip handle 330 to an FICS support catheter 320 and coaxially inserting an FICS PTA catheter 310 through the assembled support catheter/lock-grip handle so that the inflatable member 305 can be positioned and locked to expose an adjustable length of the inflatable member 141. In this configuration, the length of the exposed inflatable member 305 represents the lesion-length selective portion of the FICS LLS PTA catheter configuration. When assembled with the FICS support catheter, the balloon length can be specifically adjusted in vivo to be proportional to the target lesion length, enabling effective lesion treatment. By adjusting balloon length and appropriate inflation pressure, physicians can deploy a PTA balloon with an inflated portion adjusted to correspond to the length and texture of a hypothetical lesion. The adjustable FICS configurations increase the quality of treatment, resulting in a reduced frequency of dissections, an increased procedural efficacy, and reduced procedural times and costs. In this configuration, the FICS lock-grip handle 320 stabilizes the position of the outer sheath formed by the FICS support catheter 310 relative to the position of the FICS LLS PTA catheter by preventing movement, or recession, of the FICS support catheter 310 during balloon dilatation.

Figure 9:
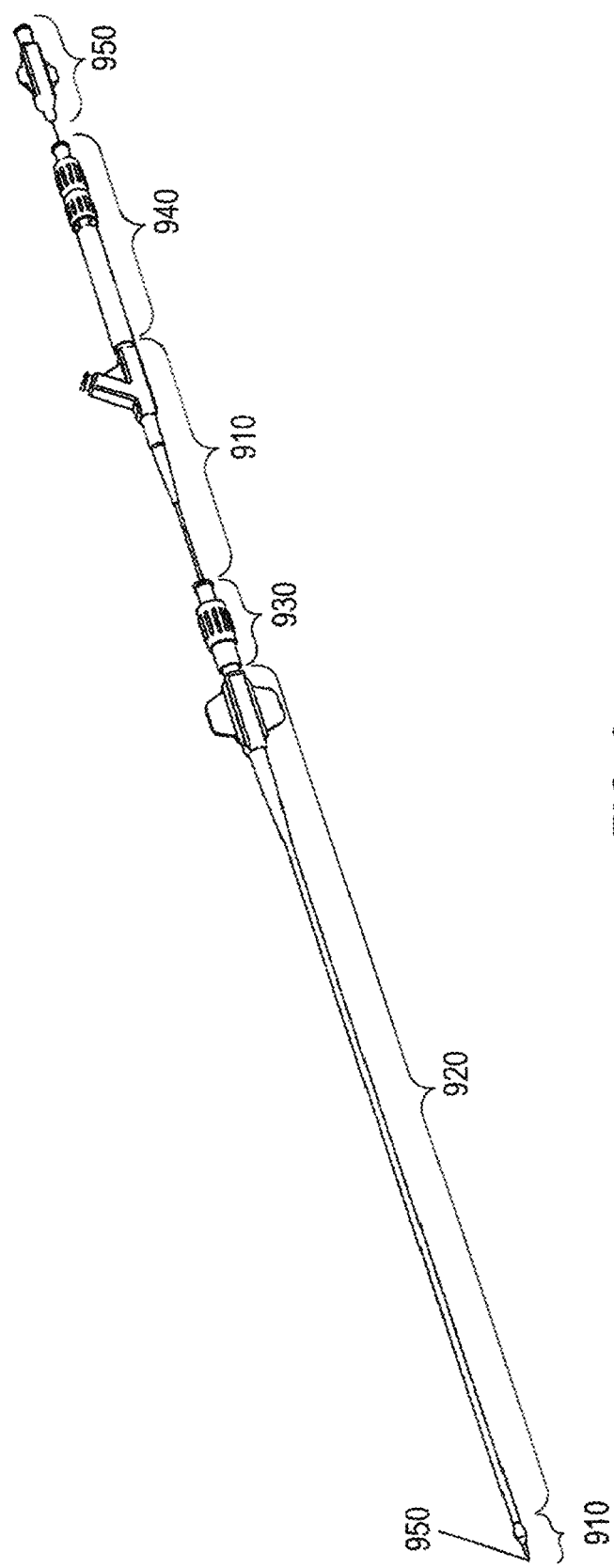
FIG. 9 illustrates a perspective view of an FICS dilator assembled with the FICS PTA Catheter, forming a steerable LLS & hypotube dilator tip.

FIG. 9 illustrates a perspective view of an FICS dilator assembled with the FICS PTA catheter, forming a steerable LLS & hypotube dilator tip. As shown in FIG. 9, the dilator configuration is assembling from functional units shown in FIG. 1. The FICS support catheter 920 is deployed over a pre-disposed guidewire, a hemostatic valve 930 is connected to the proximal end of the FICS support catheter, a FICS PTA catheter 910 with an inflatable member at the tip for anchoring into a target vessel adjacent to the CTO cap is inserted into the FICS support catheter, and a lock-grip handle 940 is connected to the FICS PTA catheter, and an FICS dilator 950 that can incorporate a distal CTO penetration or reentry tip is inserted into the FICS PTA catheter. The balloon portion can be contained within an outer sheath formed by the FICS support catheter. In this configuration, the FICS lock-grip handle 1040 stabilizes the position of the outer sheath formed by the FICS support catheter 1020 relative to the position of the FICS LLS PTA catheter by preventing recession of the FICS support catheter 920 during balloon dilatation. Length adjustment is facilitated by a lock-grip handle that serves as a displacement and locking element. The lesion-length-selectivity property of the FICS LLS PTA Dilation Catheter enables length-customizable vessel centering and anchoring, in contrast to fixed length inflatable dilator configurations, with an additional benefit that the FICS LLS PTA catheter configuration is already assembled, in place, to enable consecutive treatments.

1.3 an Overview of Multiple FICS Configurations that can be Selectively Configured by Clinicians FIG. 15 provides an overview of various FICS configurations. FIG. 15 provides a visual map of the various functional units and functional subunits that can be selectively combined by a clinical operator for constructing configurations effective for treating a broad range of complex lesions and CTOs. Solid-framed boxes and solid arrows in FIG. 15 indicate combinations of functional units and functional subunits that can be effective for a particular therapeutic application. The dashed boxes and dashed arrows included in FIG. 15 indicate alternative combinations of functional units and functional subunits that may be configurable for particular clinical situations.

The chart shown in FIG. 15 indicates certain configurations that can be selectively assembled by clinical operators as suitable for patient-specific situations. Starting at the top left of the diagram, 1500 represents an FICS configuration that combines assemblies (1510) of various functional units (1520) and functional subunits (1530). Three FICS configurations in alignment with 1510 are shown as solid boxes. Configuration 1511 represents an FICS LLS PTA configuration as shown in FIG. 3. Configuration 1512 represents an FICS CTO-dilator configuration as shown in FIG. 2). Configuration 1513 represents an FICS reentry-dilator configuration, shown in FIGS. 2 and 9.

The FICS LLS PTA configuration 1511 can be assembled by combining an FICS support catheter 1521, an FICS PTA catheter 1523, and an FICS lock-grip handle 1524. The dilator 1522 is represented by a dashed box to indicate that this functional unit may be temporarily employed during the maneuvering of the support catheter 1521 and/or may be optionally included for user convenience. For example, the dilator 1522 can be inserted into the support catheter 1521 for effecting atraumatic maneuvering of the support catheter over the guide wire prior to employing the FICS LLS PTA configuration.

The FICS CTO-dilator configuration 1512 can be assembled by combining an FICS support catheter 1521, an FICS PTA catheter 1523, and an FICS lock-grip handle 1524. The PTA catheter 1523 is represented by a "dashed" box to indicate that this functional unit is optional, such as during the deployment of a dilator configuration. The PTA catheter 1523 is not part of the dilator configuration because PTA deployment becomes applicable only after achieving CTO penetration. In addition to selecting these functional units, the clinical operators may select from several FICS-dilator design options, each incorporating a different distal-tip design suitable for a particular therapeutic application, by selecting one of: a non-inflatable, basic dilator tip 1534 without anchoring and centering functionality, or, in other words, without an inflatable member, a non-inflatable; a reinforced dilator tip 1535 without anchoring and centering functionality; a non-anchoring/non-centering basic dilator tip with a coaxially embedded hypotube 1536; and an inflatable dilator tip with a coaxially embedded hypotube 1537 with anchoring and centering functionality. The design options including a hypotube provide an additional directional/rotational steering capability about the length axis. Furthermore, a clinical operator may select from several dilator tip designs, each comprising a hypotube tip, formed as a lancet, having either a non-malleable, blunt-ended tubular member incorporated as a CTO penetration tip 1742 or a malleable, tubular member 1745 embodied with a cutting edge. Furthermore, an FICS dilator incorporating tip design 1542 can be combined with additional functional units, such as the support catheter and the PTA catheter, for constructing configurations for intraluminal recanalization.

The FICS reentry-dilator configuration 1513 can be assembled by combining an FICS support catheter 1521, an FICS PTA catheter 1523, and an FICS lock-grip handle 1524. A PTA catheter 1523 is represented by a dashed box as an optional functional unit. Clinical operators may select from several FICS-dilator design options, each incorporating a different distal-tip design, by selecting from a non-anchoring/non-centering basic dilator tip with a coaxially embedded hypotube 1536 and an inflatable dilator tip with a coaxially embedded hypotube 1537 with anchoring and centering functionality. Tip-design options that include a hypotube provide an additional directional/rotational steering capability about the length axis. Furthermore, clinical operators may select from several dilator-tip designs, each comprising a hypotube tip, formed as a lancet, having either a non-malleable, blunt-ended tubular member 1742 or a malleable, tubular member 1745 with a cutting edge incorporated as a reentry tip. An FICS dilator incorporating tip design 1745 can be combined with additional functional units, such as the support catheter and the PTA catheter, for constructing configurations for performing extraluminal recanalization.

An FICS dilator can be used to perform intraluminal and/or extraluminal recanalizations during lesion-length-selective, multi-stage dilations. Several alternative designs for the dilator are obtained by incorporating one of, a non-inflatable, distal polymeric member without anchoring and/or centering functionality; an inflatable, distal polymeric member exhibiting anchoring and/or centering functionality; a mechanically actuated, hypotube tip coaxially incorporated in at least a portion of the distal polymeric member, capable of translational movement; and a mechanically actuated, hypotube tip coaxially incorporated in the distal polymeric member, capable of translational and rotational movement. The hypotube member can be joined with a dilator hub and the hypotube distal-tip portion can be formed as a CTO penetration tip, as a reentry Tip, or as a tip conferred with both functionalities. An inflatable, polymeric member can be formed by combining a support catheter and a PTA catheter. CTO-dilator and/or reentry-dilator configurations may include a support catheter; a PTA catheter; a lock-grip; and a hypotube formed with a CTO penetration tip and/or a reentry tip. The lock-grip may include a spring-loaded mechanism for mechanical actuation of the hypotube member.

2. Functional Unit Subassemblies 2.1. FICS Lock-Grip

Figure 4:
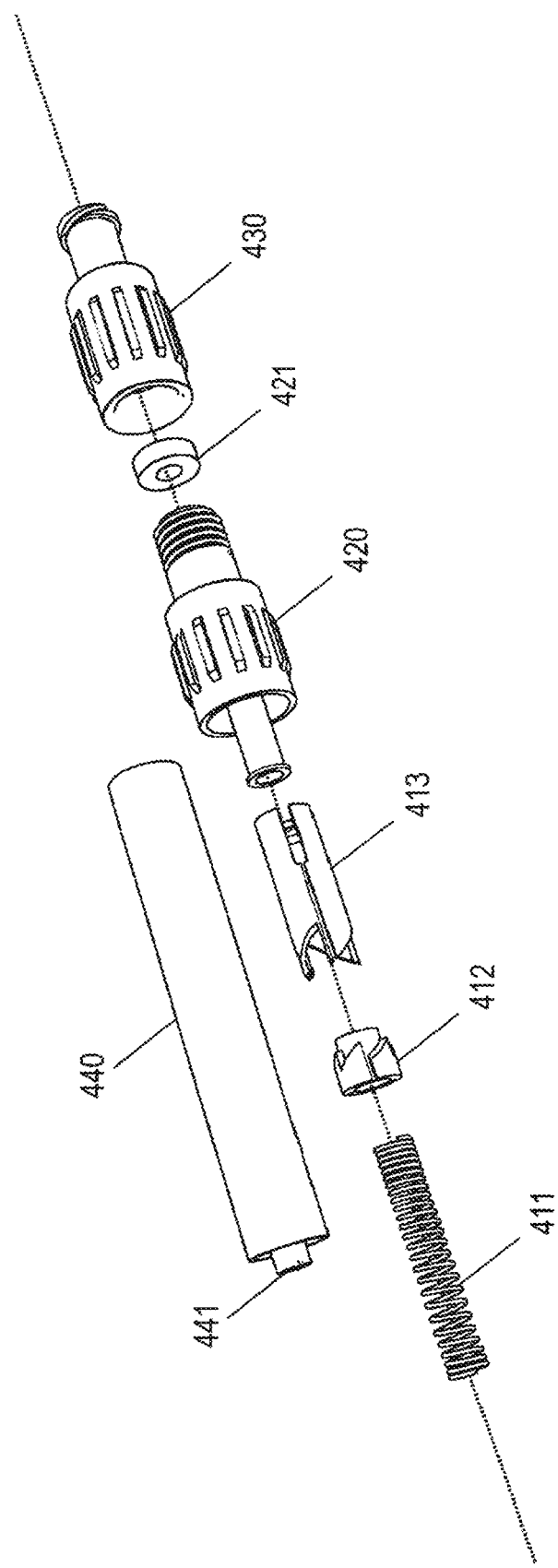
FIG. 4 is a perspective diagram illustrating the internal components of an FICS lock-grip handle.

FIG. 4 is a perspective diagram illustrating the internal components of an FICS lock-grip handle. In FIG. 4, the FICS lock-grip handle comprises, from left to right: a spring element 411, a lower cam body 412, an upper cam body 413, a connector component 420, a hemostatic valve 421, and a shaft-locking handle 430. The spring element 411, the lower cam body 412, and the upper cam body 413 can be enclosed within an external casing member 440 with a distal connector element 441. The connector component 420 can be coupled/connected to a shaft-locking handle 430, and the joined 420/430 unit can serve as a pushing handle for engaging the mechanical actuation mechanism (411, 412, and 413) contained within the external casing 440. Mechanical engagement between the mechanical actuation mechanism (411, 412, and 413) of the FICS lock-grip and the shaft member of the FICS dilator or FICS LLS PTA catheter can occur when the lower cam 412 is mechanically engaged with the upper cam 413.

An FICS lock-grip handle is a component of the FICS dilator configuration and the FICS LLS PTA catheter configuration. An FICS lock-grip handle enables the shaft member of either an FICS dilator or an FICS LLS PTA catheter to be coaxially engaged with the FICS support catheter so that the distal tips of either functional units can be projected controllably in vivo through the distal end of the support catheter towards a target occlusion, plaque, or lesion for achieving successful circumnavigation or penetration. An FICS lock-grip handle can mechanically engage/disengage the shaft portion of either an FICS dilator or an FICS LLS PTA catheter so that relative translational movement and positioning of these components with respect to an FICS support catheter is enabled. An FICS lock-grip handle provides hemostatic sealing across the outer shaft portion to prevent excessive bleeding during device operation.

A shaft member of an FICS dilator or an FICS LLS PTA catheter can attach reversibly to the lock-grip components 420 and 430 via compressible seal 421 contained within the lock-grip handle. To completely remove the FICS dilator or FICS LLS PTA catheter, the lock-grip handle is un-locked, or disengaged, and the shaft is pulled out of the support catheter, for example, after completion of a CTO recanalization procedure. Independent integration of a spring-loaded tip-actuation mechanism and shaft-locking mechanism into the lock-grip handle enables the operation of a single integrated device. The integrated device is used to independently facilitate hemostatic sealing in order to control/restrict blood flow through a treated vessel during an interventional procedure, mechanically engage/lock a shaft member to a FICS support catheter, to mechanically project a dilator tip into a target occlusion/plaque/lesion, and to transport fluid through an affected vessel to diagnostically visualize an interventional outcome and/or to effect adjunct therapies. The mechanical actuation mechanism can be dimensionally configured to co-axially accommodate either an FICS dilator, for enhancing the positional control over the dilator tip, or an FICS PTA catheter, for enhancing the extension range of the PTA inflatable member. The FICS lock-grip can be maintained at a proximal hub section of an FICS support catheter throughout intervention stages. For tip propagation, however, controllable projection/translation of additional FICS functional units, such as an LLS PTA catheter, can be mechanically actuated via the same spring mechanism, with each incremental distance in tip propagation triggered by incremental spring compression, resulting in incremental exposure of an inflatable member portion.

2.2. Lock-Grip Actuation/Dilator-Tip Propagation Mechanisms

FIGS. 5A-B illustrate cross-lateral views of a first dilator-tip propagation mechanism connected to the proximal end of an FICS support catheter. FIG. 5A shows a dilator-tip propagation mechanism in a tip-retracted position, in which the dilator tip of the FICS dilator is withdrawn within the distal end of the FICS support catheter. By contrast, FIG. 5B shows the dilator-tip propagation mechanism in a tip-extended position, in which the dilator tip of the FICS dilator is extended from the distal end of the FICS support catheter. FIGS. 5 A-B represent two different position of the dilator-tip propagation mechanism that can be mechanically actuated by loading or releasing tension on a co-axially positioned spring member.

The spring-actuated mechanism can be encased within a cylindrical outer casing 530, represented as a rectangular cross-section in FIGS. 5A and 5B. The outer casing 530 can be shaped to form two compartment sections having different functionalities: a first internal compartment 528 at the distal end of the outer casing 532 can be shaped as a distal connector element 531 capable of operably engaging/connecting with a proximal hub portion 512 of a support catheter 510 and a second internal compartment 529, at the proximal end of the outer casing 534, can be shaped to co-axially align the spring-actuated dilator-tip propagation mechanism components. The second internal compartment can include a barrier member 570 in contact with a portion of the inner luminal surface of the second internal compartment. The second internal compartment has a uniform radial diameter to enable the co-axial movement of a co-axially positioned spring member 550, during spring expansion and compression cycles. The second internal compartment contains the spring member 550, which is mechanically coupled to a lower cam 540, in turn mechanically coupled to an upper cam 560. When the upper cam 560 is mechanically engaged with the lower cam 540 by applying a force towards the lower cam 540, both cams move as a unit, as when a handle portion 544 of the distal hub 543 is pressed down once, causing the combined upper and lower cams move together. The upper cam 560 is connected to hypotube member 520 so that when the lower and upper cams are moved as a unit with respect to the spring 550, the dilator tip positioned at the distal end of the hypotube member 520 moves accordingly in the same direction as the movement of the cams 560 and 540. Both cams can be either moved away from the co-axial spring 550, increasing the length of the spring as the spring relaxes and resulting in the tip-retracted position shown in FIG. 5A), or pushed against the co-axial string 550, reducing the length of the spring as the spring compresses, resulting in the tip-extended position as shown in FIG. 5B. Displacement of the spring member 550 is measured by a difference ΔL between the tip-retracted (FIG. 5A) and tip-extended (FIG. 5B) positions. The range of movement for the cams can be limited by a notch or protrusion member 542 on the upper cam 540 that makes contact with the barrier member 570 to limit the spring compression. Alternatively, the protrusion member 542 makes contact with a proximal stopping member 534 to stabilize the upper cam 560 and attached components.

FIGS. 6A-B illustrate cross-lateral views of a second dilator-tip propagation mechanism connected to the proximal end of the FICS support catheter. FIG. 6A shows the second dilator-tip propagation mechanism in a tip-retracted position, in which the dilator tip of the FICS dilator is withdrawn within the distal end of the FICS support catheter. In contrast, FIG. 6B shows the second dilator-tip propagation mechanism in a tip-extended position, in which the dilator tip of the FICS dilator is extended from the distal end of the FICS support catheter. FIGS. 6 A-B represent two positions of the "dilator-tip propagation mechanism" that can be mechanically actuated by loading or releasing tension on a co-axially positioned spring member.

The spring-actuated tip-propagation mechanism of FIGS. 6 A-B can be encased separately from a locking handle 680 shaped to form a hemostatic valve portion capable of mechanically and operably engaging/connecting with an external surface portion of the hypotube 620. This is in contrast to the hypotube attachment mechanism shown in FIGS. 5 A-B. The second tip-propagation mechanism combines a tip actuation mechanism and a shaft-locking mechanism to independently facilitate hemostatic sealing; mechanical locking; and tip extension at substantially the same or different time points.

The spring-actuated mechanism can be encased within an outer casing 630, shown as a rectangular cross-section in FIGS. 6A and 6B. The outer casing 630 can be shaped to form two compartments having different functionalities: a first internal compartment 628 at the distal end of the outer casing 630, shaped as a distal connector element 631 capable of operably engaging/connecting with a proximal hub portion 611 of the support catheter 610; and a second internal compartment 629 at the proximal end of the outer casing 630, shaped to co-axially align the spring-actuated dilator-tip propagation mechanism components. The second internal compartment includes a set of guiding surface elements 670 (e.g. channels, grooves, tracks) along a portion of the inner luminal surface of the second internal compartment. The second internal compartment has a uniform radial diameter to enable the co-axial movement of a co-axially positioned spring member 650. The second internal compartment contains the spring member 650, which can be mechanically coupled to a lower cam 640, which can be mechanically coupled to an upper cam 660. Both upper and lower cam bodies can be in mating contact with the guiding surface elements 670 to enable guided translational movement of the cam shaft components along a desired length portion within the casing 630. The upper cam body 660 can be translated beyond the position of the surface element portion 670, causing it to rotate to a different cam shaft height. The lower cam 640 can be connected to the hypotube member 620. The hypotube member 620, at the proximal end, is extended through both cams and through the first handle 644, passing through a locking handle 680. The locking handle 680 includes a compressible seal 681 so that, when connected to member 645, the compressible seal 681 expands radially to seal any space between the components to prevent blood flow from the catheters. The hypotube 620 can be reversibly attached to the upper cam shaft via the compressible seal 681 contained within the locking handle 680 so that the hypotube 620 can be operationally coupled to the tip-actuation mechanism. The FICS dilator is formed from a hypotube having a shaft member 620. The hypotube shaft is mechanically coupled to the lower cam body 640 by an elastomeric/compressible seal 681. The seal 681 is compressed by rotating/screwing the handle 680 onto the lower cam body 640. Because the hypotube is relatively stiff/rigid, any translational movement of the hypotube shaft is directly translated into dilator tip movement.

3 FICS Dilator and Tip Configurations

3.1. FICS Dilator

FIGS. 7A-D illustrate cross-lateral views of four mechanically actuatable FICS dilator tip configurations. An FICS dilator can be provided preconfigured with various features enhancing the convenient operability of the FICS dilator in designated functional configurations. The FICS dilator can be provided with anchoring/centering functionality (FIG. 7D) or without anchoring/centering functionality (FIGS. 7 A-C). A projectable tip portion can be provided with steering functionality (FIGS. 7 C-D) or without steering functionality (FIGS. 7 A-B). Finally, an FICS dilator can be provided as a CTO dilator or as a reentry dilator, depending on the tip configuration. An FICS support catheter can be combined with an FICS dilator to produce an FICS CTO-dilator configuration having a CTO penetration tip, as shown in FIGS. 7 A-B, FIGS. 7 C-D, and FIG. 8A, used for performing intraluminal CTO recanalization. In certain implementations, a hypotube body that can be shaped as a CTO penetration tip, as shown in FIG. 8A, can be replaced by a hypotube body adapted with a reentry tip, as shown in FIG. 8B, to yield the FICS reentry-dilator configuration shown in FIGS. 7C-D. The FICS reentry-dilator configuration is incorporated into the functional unit assembly shown in FIG. 2 and FIG. 9 for performing extraluminal CTO recanalization via subintimal access and reentry.

In general, an FICS dilator can be designed to include a specifically configured, mechanically projectable tip constructed from a concentrically positioned hypotube to facilitate enhanced intra- and/or extraluminal recanalization of chronic total occlusion and a tapered, polymeric sleeve or shaft portion to provide a seamless transition from a guide wire to the distal end of an FICS support catheter for enabling enhanced, atraumatic passage, guidance and support. FICS dilators are configured for inter-operability with FICS support catheters, which can provide substantial structural guidance and support as an external tubular shield. With respect to the exemplary FICS dilator tip configurations described below, in FIGS. 7-8, the FICS dilator tips can remain receded within the guide-wire lumen compartment of the FICS dilator seated within the FICS support catheter to shield the vessel walls during transport and maneuvering operations to avoid potential vessel damage.

Figure 7A:
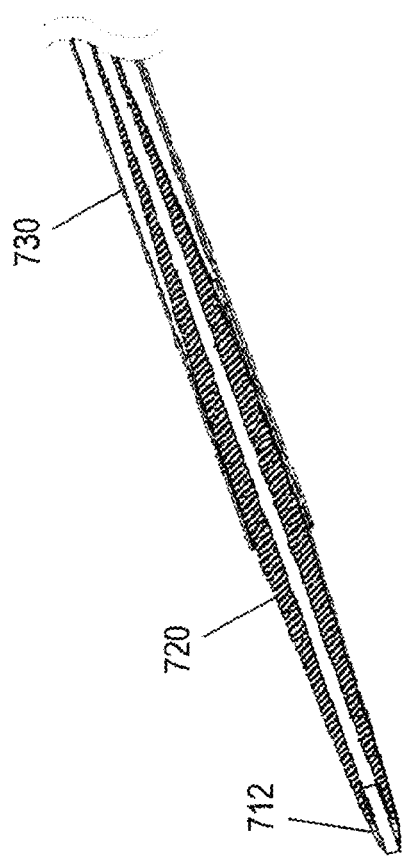
FIGS. 7A-D illustrate cross-lateral views of four mechanically actuatable FICS dilator tip configurations.
Figure 7C:
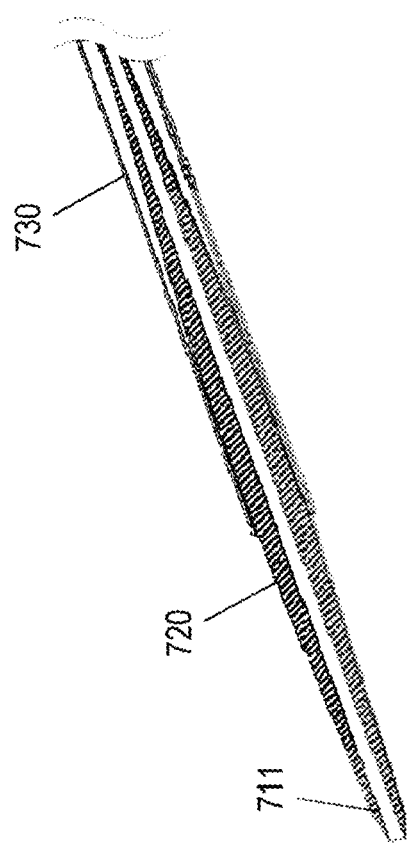
Figure 7B:
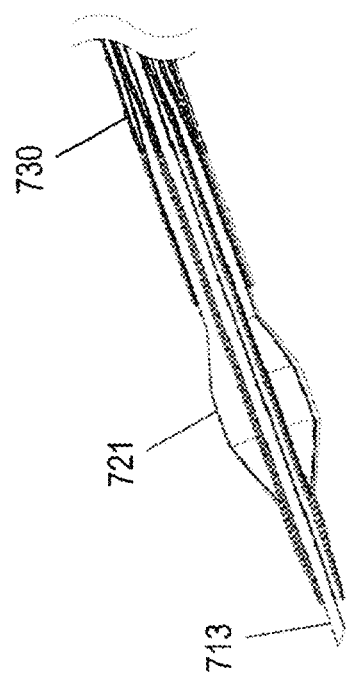
Figure 7D:
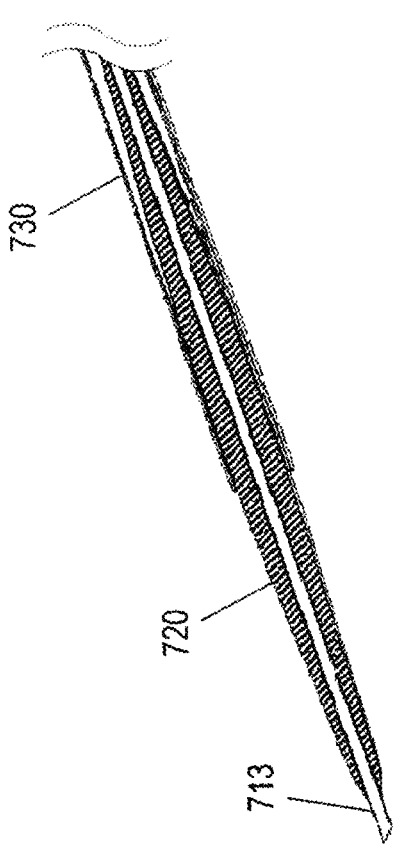
Figure 8B:
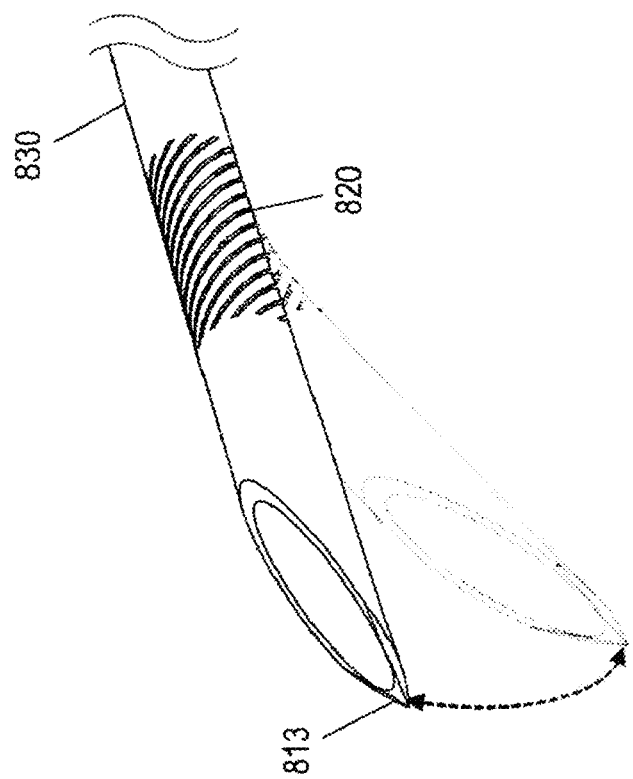
FIGS. 8A-B illustrate exemplary dilator tip designs for facilitating intraluminal and extraluminal recanalization.
Figure 8A:
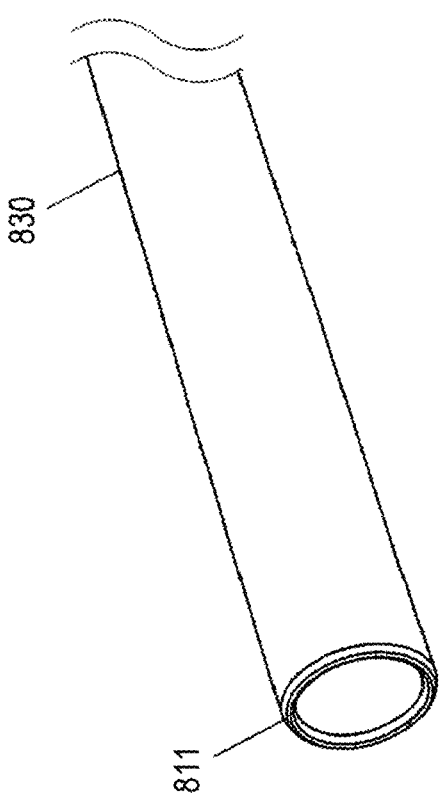

FIG. 7A shows a basic CTO penetration tip 711 fused against a single-lumen, non-inflatable polymer member 720, with the tip portion exhibiting a constant circumference along a tip-length portion. The tip portion 711 and 720 of the FICS dilator exits from the distal end of the FICS support catheter 730. The CTO penetration tip can be formed as an elongated polymeric body 720, comprising a distal, tapered tip portion 711 and having a section of uniform radial circumference for insertion into an outer support catheter sleeve 730. FIG. 7B shows a reinforced CTO penetration tip that includes a hardened tip section 712, which can be formed from substantially rigid materials, such as ceramics or metals, for improving CTO penetration. The tip section is inserted into the polymeric body 720. In FIG. 7C, a basic & hypotube tip used as a reentry-tip configuration differs from the basic-tip configuration by incorporating an additional, coaxially alignable hypotube element 713 within a polymeric body 720. In FIG. 7D, an LLS & hypotube tip used as a reentry-tip configuration combines a coaxially insertable hypotube element 713 and an inflatable member 721 of an FICS LLS PTA catheter. Alternatively, the reentry-dilator tip 713 can be seamlessly fused to a radially expandable polymer member having two lumens 720, with the tip portion exhibiting an expandable diameter. The tip portion 713 and 720 of the FICS dilator exits from the distal end of an FICS support catheter 730.

This expandable configuration shown in FIG. 7D can be adjusted to fit vessels of variable diameters. The radially expandable polymer member 720 can serve as a centering balloon for improving vessel-anchoring capability for effective coaxially aligned penetration by the CTO-penetration dilator tip and guide wire passage through the CTO and/or for effective orientation-stabilized subintimal access/reentry of the reentry-dilator tip and extraluminal recanalization.

3.2. FICS CTO-Penetration and Reentry TIPs

FIGS. 8A-B illustrate exemplary dilator tip designs for facilitating intraluminal and extraluminal recanalization. FIG. 8A shows a CTO penetration tip comprising a non-malleable and blunt-ended hypotube of an FICS dilator suitable for intraluminal recanalization. FIG. 8A shows a CTO penetration tip of FIGS. 7C-D formed from a hollow-bore hypotube, having a substantially elongated tubular member 830 and a blunt-edged tip 811. The CTO penetration tip can be formed from a combination of one or more substantially rigid ceramic, polymeric or metal-based materials to enable puncture and subsequent penetration of hardened, calcified CTO cap regions. The tip can be independently formed from, or jointly affixed to, a hypotube to further increase pushability while preventing or reducing potential bending, buckling, or kinking of the distal dilator shaft segment during CTO penetration. A FICS dilator with a CTO penetration tip may be used in clinical situations in which direct CTO passage is carried out during intraluminal recanalization.

FIG. 8B shows a reentry tip comprising a malleable and angled hypotube of the FICS dilator, suitable for extraluminal recanalization. In FIG. 8B, the reentry tip differs from the CTO penetration tip shown in FIG. 8A by incorporating a substantially malleable hypotube segment 820 that can be precisely cut, as a slotted-tube or in a spiral pattern, into the hypotube member 820 and positioned. An FICS dilator with a reentry tip can be used in clinical situations in which direct CTO passage is undesirable. An FICS dilator with a reentry tip can be utilized to prepare for percutaneous intentional extraluminal recanalization, referred to as a "reentry procedure," which involves creating a directional cut into the subintimal tissue layer in the vicinity of a target CTO, crossing the opening with a guide wire, creating a second directional cut in the subintimal tissue layer in the vicinity of the CTO, crossing the opening with a guide wire so that the CTO can be extraluminally circumnavigated, performing a reentry into the true lumen of the vessel, dilating an artificial extraluminal passage; and restoring perfusion through the affected vessel. The exposable hypotube tip section can be provided with a straight, angled, or shapeable tip orientation. The hypotube flexible tip may be shaped ex vivo by a physician, for example by utilizing a pre-shaping tool, and loaded in a pre-tensioned state into a dilator/LLS via a coaxial arrangement. By exposing the pre-tensioned segment, for example, by mechanical tip propagation, the tip can assume a configuration in vivo to facilitate optimized subintimal tissue penetration. The tip can be formed out of a plastically/elastically deformable metal alloy. Alternatively, by forming the tip out of a pseudoelastic or superelastic alloy, including Nitinol, beneficial shape memory effects can be utilized. The edge of the tip can be formed by precision cutting and polishing, and can be variably angled, for example, obtusely or acutely angled relative to the length axis, to achieve a variably blunted or sharpened tip for improved shaft pushability and for efficiently cutting into a subintimal tissue layer in a directionally guidable manner.

In general, the mechanically projectable hypotube tip sections can be provided with a straight, angled, or malleable tip. The edge of the distal tip can be formed through processes of precision cutting and polishing, or can be variably angled to achieve a variably blunted or sharpened tip for improving shaft pushability, directional control, and cutting efficiency into a CTO and/or into subintimal tissue during penetration. As an embodiment, the flexible reentry tip can be blunt-edged to minimize the risk of vessel perforation during subintimal access. In other implementations, the CTO penetration tip may be provided with a flexible segment to enable simultaneous CTO penetration and/or reentry. The inner tubular member forming the hypotube may comprise a combination of metals and polymers. The dilator tips can be actuated by a spring mechanism incorporated in the FICS lock-grip handle. The FICS dilator unit can be configured for simultaneous operation of the FICS support catheter, which can provide substantial structural guidance and support as an external tubular shield. The FICS dilator can be placed within the lumen compartment of the FICS support catheter to shield either a CTO penetration or a reentry tip during transport through the affected vessel, thereby minimizing potential vessel wall damage.

Figure 10:
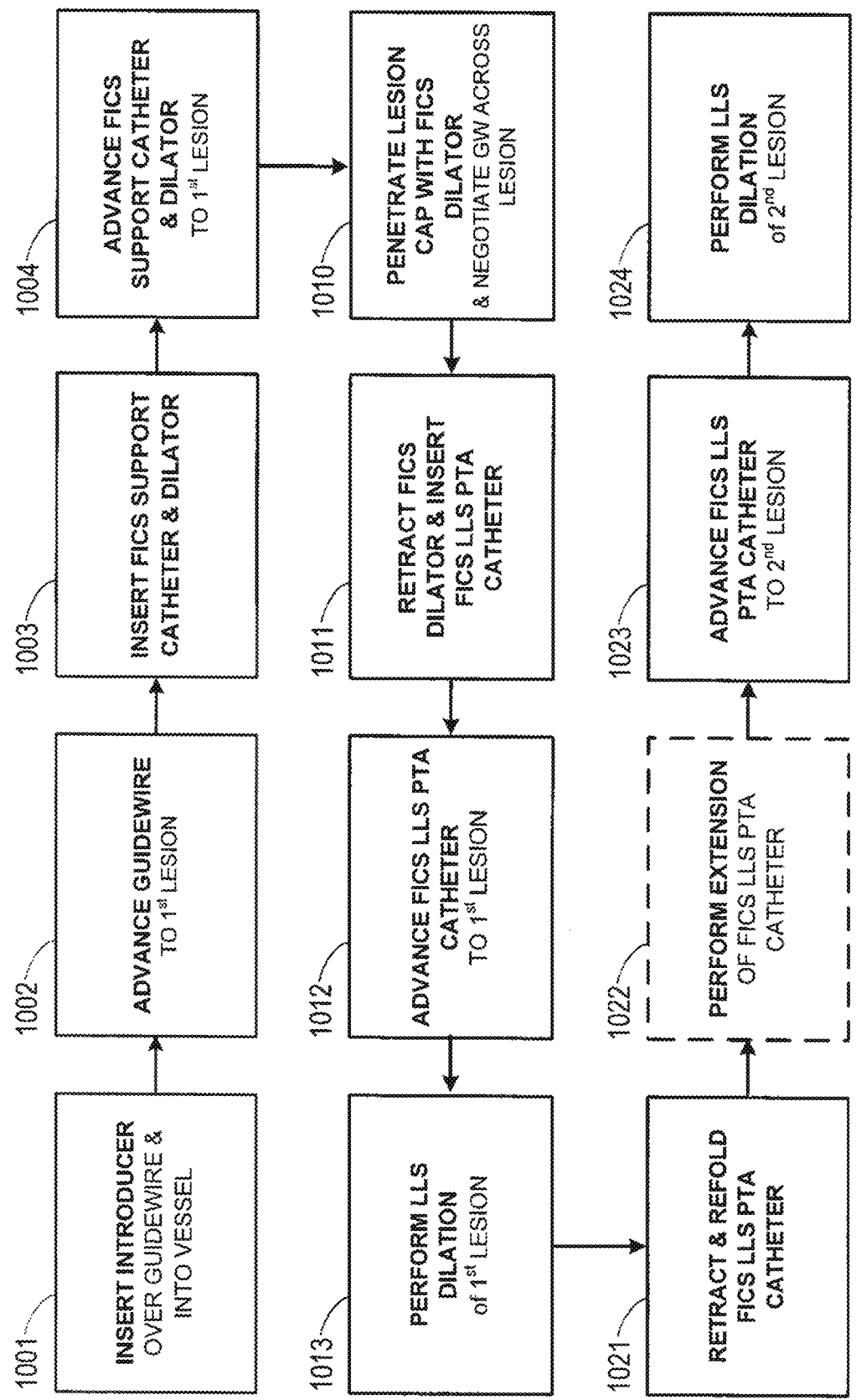
FIG. 10 is an exemplary flow diagram of a multi-staged angioplasty procedure performed in vivo for successive therapeutic treatment of complex lesions and CTOs utilizing the FICS.

4. Operational Characteristics of FICS 4.1 FICS LLS PTA Dilator Configurations with Lesion-Length Selectivity for Multi-Staged Procedures FIG. 10 is an exemplary flow diagram of a multi-staged angioplasty procedure performed in vivo for successive therapeutic treatment of complex lesions and CTOs utilizing the FICS. In FIG. 10, as the first step 1001, an introducer sheath is inserted to enable vascular access of catheter devices under hemostatic conditions. In step 1002, a predisposed guide wire is controllably advanced to a target treatment area and positioned across the lesion. In step 1003, an FICS support catheter is inserted simultaneously with an FICS dilator through the lumen of the introducer sheath and over the predisposed guide wire. In step 1004, the FICS support catheter and FICS dilator are controllably and simultaneously advanced over the prepositioned guide wire to a first intended treatment area, such as a first hypothetical complex lesion. In step 1010, an FICS dilator tip is controllably advanced into a hardened surface cap of a CTO to facilitate guide-wire negotiation and CTO penetration. In step 1011, the FICS dilator is retracted, and an FICS PTA catheter is inserted. In step 1012, the FICS PTA catheter is controllably advanced via the predisposed FICS support catheter and over the predisposed guide wire to a first, complex lesion. In step 1013, the distal working end of an FICS LLS PTA catheter is used to length-selectively treat the lesion and restore luminal patency at the first intended treatment site. This step enables the angiographic visibility of lesions distally located in the affected vessel. After deflating and retracting the length selective balloon element back into the FICS support catheter in step 1021, the flushing holes of the FICS support catheter are used for injecting contrast agent to enable angiographic follow up. As an optional step 1022, if additional lesions are observed along the same affected vessel, the usable length portion of the FICS LLS PTA catheter is manually extended by a physician while maintaining the current position of the guide wire within the intended treatment site. The predisposed guide wire is controllably advanced to a next target treatment area and the distal end of the guide wire across the second lesion is positioned. In step 1023, the physician controllably advances the optionally extended FICS LLS PTA catheter together with the FICS support catheter over the prepositioned guide wire to the next intended treatment area, such as a second lesion. In step 1024, the distal working end of the optionally extended FICS LLS PTA catheter is used to length-selectively treat the lesion and restore luminal patency at the second intended treatment site. The number of treatment sites utilized in this flow diagram is exemplary in nature and can include an arbitrary number of successive treatment sites, provided that the length of the predisposed guide wire, the length of the support catheter, and the adjustable usable length portion of the catheter in extended configuration enables access to successive target treatment areas.

4.2. CTO Penetration by Dilator Tip Propagation

FIGS. 11A-D illustrate cross-lateral views representing four consecutive configurational stages A-D for mechanically propagating a CTO penetration tip. In FIG. 11A, a cross-lateral view of an occluded vessel 1100 amenable for treatment is shown at a first stage, including a vessel wall 1101, a hardened CTO lesion cap 1102 and softer lesion tissue 1103. An FICS support catheter 1110 is illustrated as an elongated tubular member concentrically situated in the affected vessel and positioned along the vessel length axis 1144. The FICS support catheter incorporates a radiopaque marker band 1111 located on a distal tip region, and one or more proximally positioned flushing/aspiration holes 1112, 1113, 1114. The FICS dilator is inserted into the lumen space of the predisposed and temporarily stationary FICS support catheter shaft 1110, and is positioned with respect to the length axis of the FICS support catheter so that a proximal radiopaque marker 1126 located on the FICS dilator shaft 1120 and an inflatable member 1130 are positionally aligned with a substantially similarly sized radiopaque marker 1111 located near the distal end of the FICS support catheter. Alternatively, a differently sized radiopaque marker 1125 near the tapered, distal dilator tip portion 1121 and one or more of the radiopaque markers 1111 are aligned to indicate adequate tip positioning and proper atraumatic alignment between the FICS support catheter and FICS. At this stage, it is noted that inflatable member 1130 is substantially folded within the FICS support catheter. An anchoring dilator tip configuration similar to the configuration shown in FIG. 7D is used.

In FIG. 11B, a cross-lateral view of the occluded vessel 1100 is shown at the second hypothetical stage, in which the FICS dilator shaft 1120 is transposed in parallel with the length axis of the FICS support catheter 1144 and positioned in close contact with the lesion cap 1102. The relative positions for FICS dilator and FICS support catheter can be angiographically verifiable by the equidistant positioning of the three radiopaque markers 1111, 1125, and 1126. At this stage, the inflatable member 1130 of the FICS dilator is in an uninflated state and partially extends from the FICS support catheter 1110. The extension range of the inflatable member portion can be lengthwise configured so that a desirable proximal portion remains seated within the support catheter. This particular configuration can provide improved proximal balloon cone formation and enables controllable refolding of the inflatable member upon retraction.

In FIG. 11C, the cross-lateral view of the occluded vessel 1100 is shown at the third hypothetical stage, in which the inflatable member 1130 of the FICS dilator is inflated for vessel centering and anchoring in preparation for CTO penetration. Once anchored radially in the vessel, the CTO-penetration tip 1141 of the FICS CTO dilator is fully extended by the above-described spring-actuation mechanisms in order to penetrate the hardened lesion cap 1102 in preparation for guide-wire negotiation.

In FIG. 11D, the cross-lateral view of the occluded vessel 1100 *t* is shown at the fourth hypothetical stage, in which the penetrated lesion cap 1102 is negotiated with a guide wire 1150 to facilitate guide wire crossing across the remaining lesion in preparation for lesion dilation.

4.3 Lesion Length Adaptability for Successive Multi-Stage Treatment

Figure 12A:
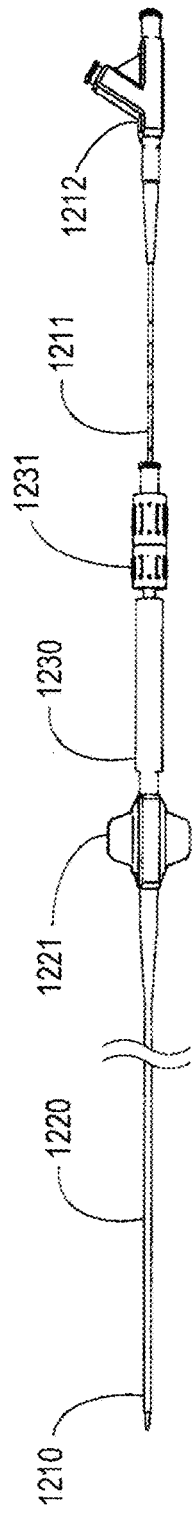
FIGS. 12A-D illustrate inter-operability of functional units during deployment of an FICS LLS PTA configuration in successive multi-level stages.

FIGS. 12A-D illustrate inter-operability of functional units during deployment of an FICS LLS PTA configuration in successive multi-level stages. In FIG. 12A, an LLS PTA catheter 1212 is coaxially inserted into an FICS support catheter shaft 1220 through the associated support catheter hub 1221 and via the attached FICS lock-grip handle 1230. The distal tip portion 1210 of the FICS LLS PTA catheter extends from the distal end of FICS support catheter shaft 1220 to form a seamless transition with the catheter shaft. The relative positions of the FICS LLS PTA catheter and the FICS support catheter end is dialed in using the mechanical-locking feature of the lock-grip handle 1231 and the surface markings 1211 present on the proximal FICS LLS PTA catheter shaft. The lock-grip handle 1231 is mechanically engaged to lock the position of the FICS LLS PTA catheter tip to ensure atraumatic passage of the FICS components along affected vessels. The configuration shown in FIG. 12A is used for advancing the FICS LLS PTA catheter to the target treatment site.

Figure 12B:
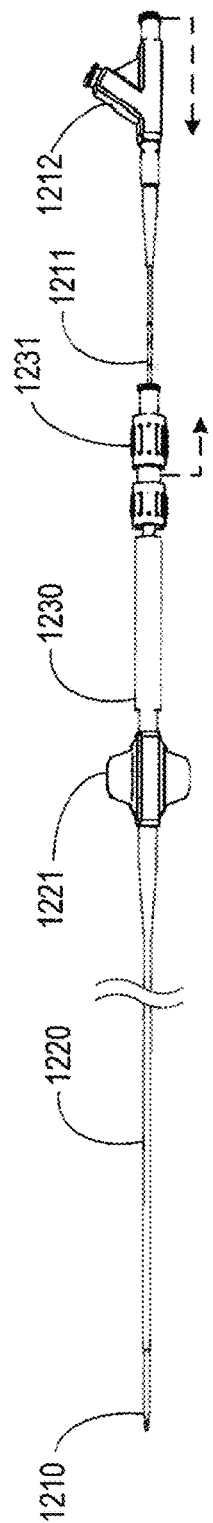
Figure 12C:
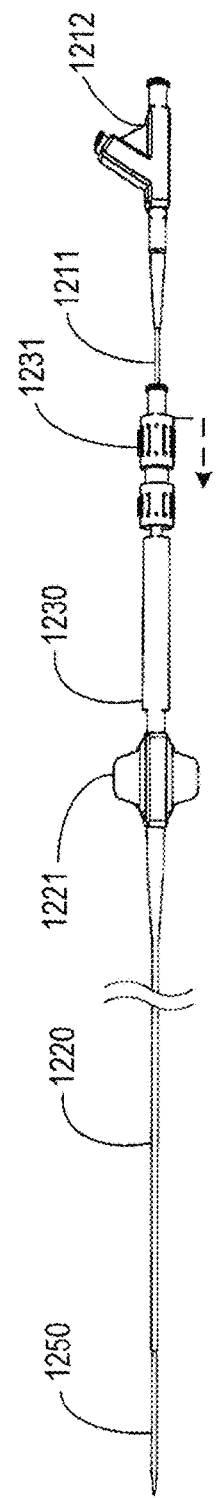
Figure 12D:
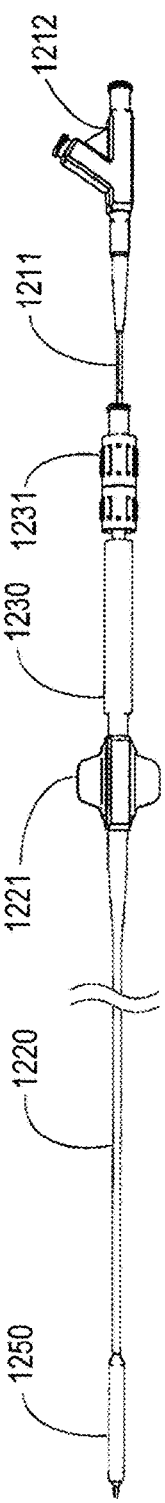

In FIG. 12B, the FICS lock-grip handle is disengaged to facilitate propagation of the FICS LLS PTA catheter through the FICS lock-grip handle and FICS support catheter. In FIG. 12C, the FICS lock-grip handle is reversibly engaged to lock the selectively exposed length portion of the inflatable member 1250. The configurations shown in FIG. 12B/12C are used for in vivo length selective adjustment of the inflatable member portion of the FICS LLS PTA catheter at the target treatment site. In FIG. 12D, the FICS LLS PTA catheter is inflated along the exposed portion. The configuration shown in FIG. 12D is used for lesion dilatation.

Figure 14A:
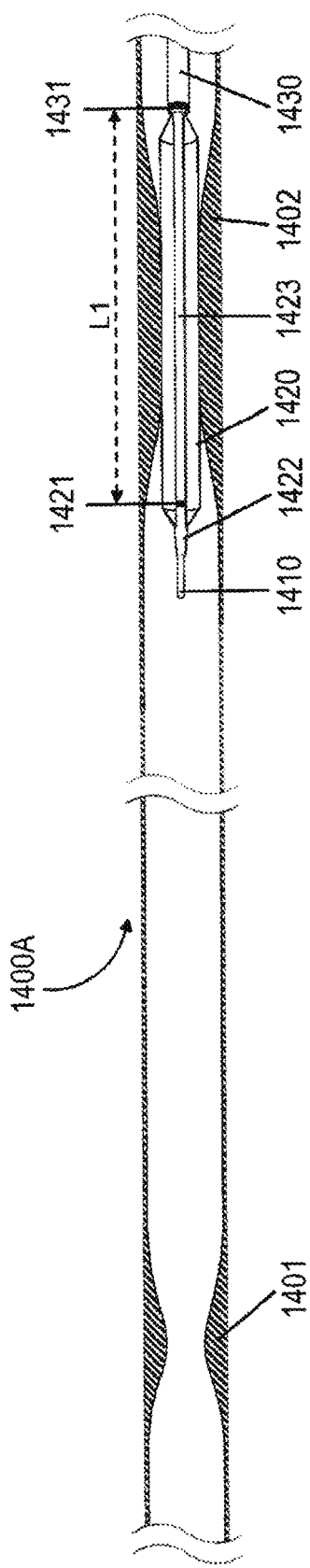
FIGS. 14A-B illustrate cross-lateral views of the in vivo lesion-length selective feature of the inflatable member for the FICS LLS PTA catheter for successive lesion treatments.
Figure 14B:
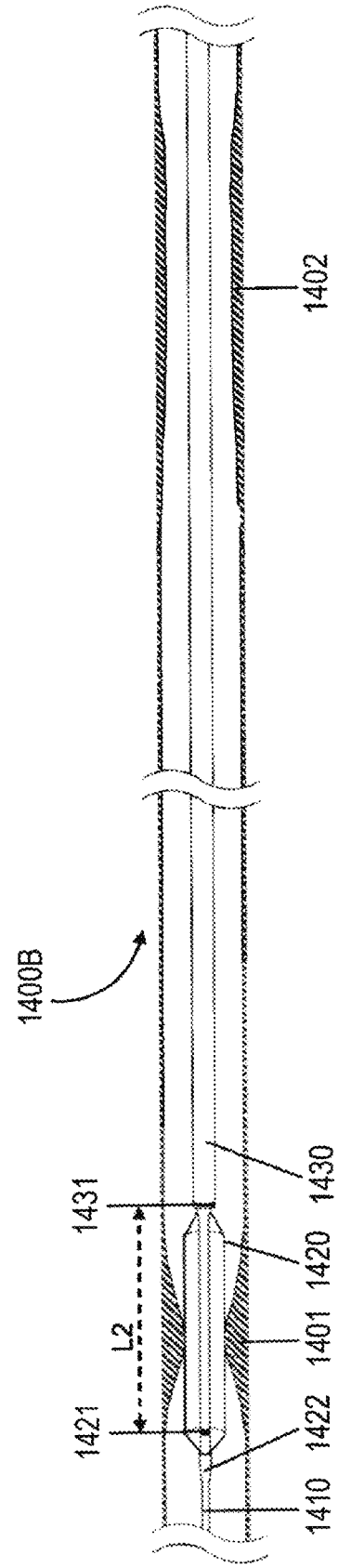
Figure 15:
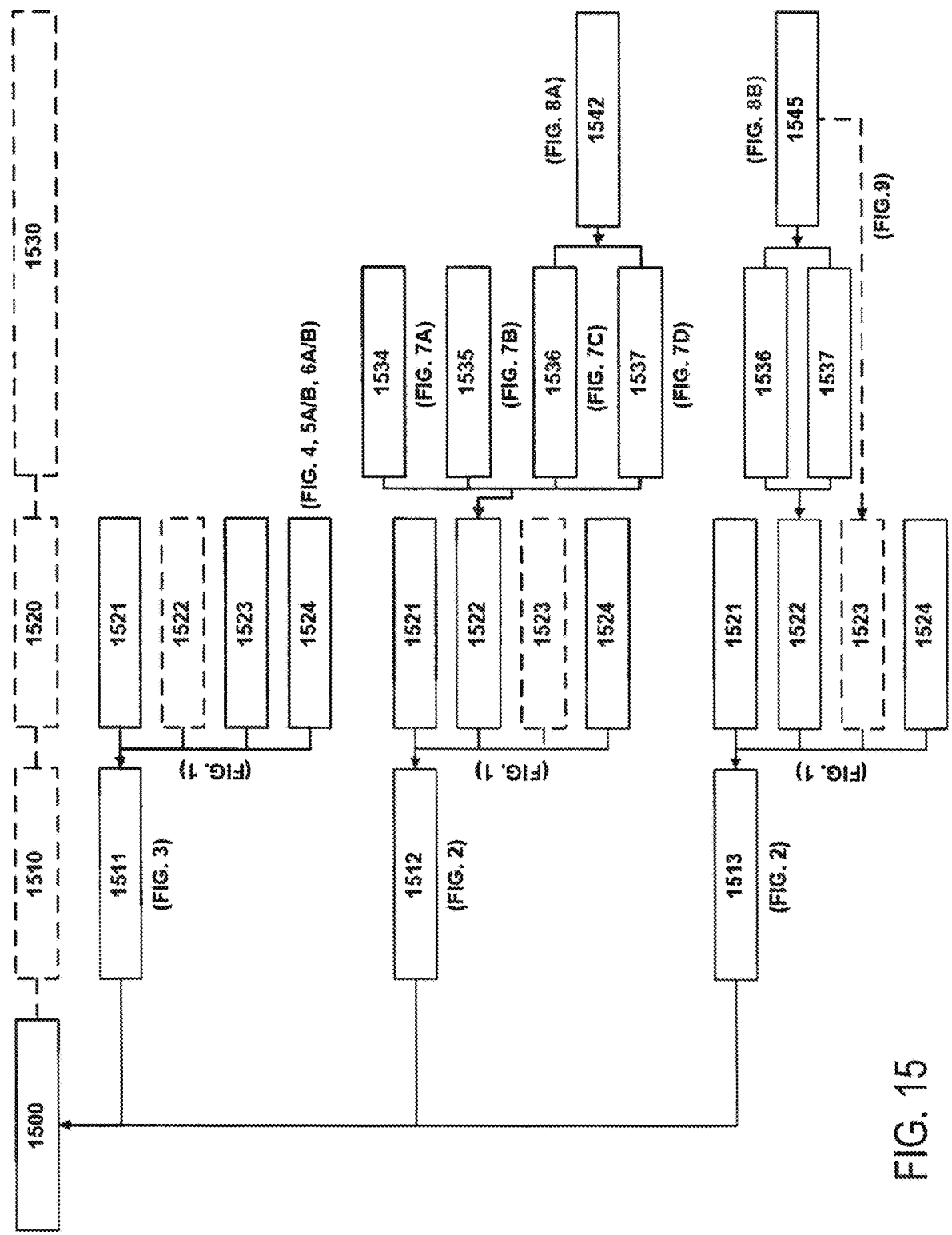
FIG. 15 provides an overview of various FICS configurations.

FIGS. 14A-B illustrate cross-lateral views of the in vivo lesion-length-selective feature of the inflatable member of the FICS LLS PTA catheter for successive lesion treatments. In FIG. 14A, a vessel 1400A is shown with a first lesion 1402 and a second lesion 1401. On the right, an inflatable member 1420 of an FICS LLS PTA catheter is exposed from the distal end of an FICS support catheter 1430. The length of the inflatable member 1420 is selectively adjusted to the length of the lesion (L1), angiographically verifiable via the distance between radiopaque markers 1421 and 1431, the first marker incorporated into a distal inflatable member portion and the second incorporated into a distal support catheter shaft portion. The inflated balloon is controllably dilated along the lesion length by radially exerting pressure perpendicular to the surface of the lesion until the recanalized lesion is widened sufficiently to restore luminal patency.

In FIG. 146, the vessel 1400B is shown after the first lesion 1402 has been treated successfully and the FICS LLS PTA catheter has been repositioned, with the inflatable member portion shown controllably extended so that the length of the inflatable member 1420 is aligned with the length of the second lesion 1401 (L2). When the balloon is dilated, pressure is radially exerted against the surface of the lesion until patency is restored in the second lesion. The procedure can be repeated as many times as necessary using the above-described FICS configurations.

5. Dimensional Characteristics of FICS

To construct therapeutic-specific configurations of the FICS of the present disclosure, the individual functional units and functional subunits of the FICS are designed so that the dimensional specifications of these components ("FICS specifications") are interoperable over a broad operational range. For example, catheters, PTA balloons, dilators, and guide wires are generally provided as a set of variable products that provide multiple sizing options for selecting instrument length and instrument diameter to cover a broad range of procedural applications. Because the FICS is intended to provide a comprehensive medical device platform for treating a broad range of complex lesions and CTOs, each of the FICS components has a dimensional operational range.

6. Manufacture and Material Selection for FICS

In general, any components of the FICS platform can be constructed by utilizing the methods known to persons skilled in the art. Dilator and/or inflatable members of both Dilator and PTA catheter can be constructed substantially in cylindrical form, having uniformly positioned mantle surfaces along a longitudinal axis, wherein the length sections shaped with a variable tapering profile can be attached to form defined cone regions of the polymeric body/balloon. The dilation elements (polymeric body/balloon) can be located at the distal end of the indwelling FICS catheter during treatment. The inflation can be typically facilitated by incorporating one or more lumens, wherein at least one lumen can be in fluid communication with the elongate, inflatable member, and wherein one or more lumen(s) can facilitate inflation and transport contrast agents and other fluids. FICS PTA catheter may comprise at least a guide wire lumen and an inflation lumen, provided as dual lumen configurations in side-by-side or coaxial (nested) arrangement. These lumen configurations can be provided as extruded tubing, forming the "inner member," as opposed to the outer member, or catheter shaft. Inner member comprising the one or more lumen and the outer member, or a catheter shaft can be designed to have a fixed length or length adjustability.

FICS functional units intended for insertion into an FICS support catheter can be designed to be guidable with a guide wire along the length of the instrument, so that the guide wire can enter at the distal tip and exit at the proximal hub. For PTA catheters, such a design can be referred to as an over-the-wire ("OTW") configuration. In contrast to OTW balloon dilation catheters, rapid-exchange ("RX") balloon dilation catheter instruments are operated with a significantly shorter guide wire length. RX catheter may contain a guide wire exit port positioned at a defined distance from the distal tip, so that the guide wire is contained only within a limited guide wire lumen length or section and does not need to extend along the entire inner guide wire lumen. Whereas normal RX ports may be configured as single, annular openings exiting from a proximal position of the guide-wire lumen through the instrument shaft, FICS RX ports of insertable functional units are constructed, in certain implementations, as slots over a portion of the shaft. Insertable FICS dilator and PTA catheter components may benefit from an RX port for enabling decreased guide-wire lengths, particularly for systems having a usable length exceeding 150 cm.

FICS catheter components can be manufactured from biocompatible, polymeric, metallic and ceramic materials. For example, the catheter components may be manufactured from aliphatic, semiaromatic, and aromatic polyamides; polyether ether ketones (PEEK); polyimides: linear and nonlinear, branched or nonbranched, low molecular weight, medium molecular weight, or high molecular weight: low density, medium density, or high density polyolefins, including polyethylene and polypropylene, silicones, thermoplastic elastomers, such as polyurethanes ("TPEs") and fluoroelastomers, polycarbonates, polyethylene terephthalate ("PET"), and combinations, including blends and copolymers of any of these materials.

FICS catheter components can also be fabricated as single layer, dual-layer, or multi-layer configurations. For dual-layer or multi-layer configurations, certain catheter elements, including, for example, the shaft and the balloon, may utilize the same material for each layer or may utilize different materials for each layer. The multiple layers can be glued, melted, or fused together with an adhesive or by employing a co-extrusion process. Alternatively, the multiple layers may not be attached or glued together, but, instead, the multiple layers may be allowed to move independently. Additionally, the durometer of the material(s) selected for each layer may be altered to further alter the performance aspects of the individual catheter components. Also, the chemical functionality and/or physical polarity of the material can be changed to enhance interfacial adhesion between the differing layers and/or to provide exposed surfaces and/or inner lumen with an increased lubriciousness or changed surface energy when in contact with a guide wire, injected liquids, or functional coatings, for example.

These chemical and physical treatments or alternations/variations may include, for example, chemical additives that can introduce chemical functionalities to the interfacial surface when added to a base polymer formulation that forms one or more layers of the catheter component. For example, these additives may include functional groups such as carboxy- and/or amino groups, which can enhance the underlying polarity of the layer and the substrate, thus facilitating enhanced adhesion and mechanical-fixation strength in between one or more layered structures of catheter components.

Other surface modifications or plasma techniques can be employed for changing the chemical and/or the mechanical properties of the underlying substrate. The plasma modification of the material(s) may affect the polarity and/or the surface energy of the balloon layer(s). Other suitable techniques may incorporate additives, adhesives and/or filling agents, which can introduce other beneficial properties to catheter materials. For example, the catheter shaft or the balloon may incorporate radiopaque elements embedded within polymeric materials to selectively increase fluoroscopic visibility at desired shaft locations. Additionally, the shaft may incorporate fluoropolymer-based filler particles/fibers to permanently decrease a frictional coefficient as compared to an untreated base-polymer formulation or activatable, single-use coatings. Furthermore, the shaft can be reinforced and may contain metal or polymer-based strands, fibers, wires, braids, meshes and/or fabrics incorporated as layers, sections, or regions into the base-shaft material.

FICS catheter components can be manufactured by following various methods known to persons skilled in the art, including single-, dual-, and or multilayer extrusion, blow molding, dip molding, deposition, or other manufacturing methods suitable for manufacturing FICS catheter components. The material for forming FICS catheters may be subjected to mechanical processes before, during or after the catheter manufacture. If an extrusion process is utilized for the manufacturing process, the tubular member for forming the shaft member can be stretched before or during the extrusion process. The temperature, the extrusion pressure, or other parameters can be changed during the manufacturing processes to affect the properties of the manufactured shaft.

EXAMPLES

Example 1

Functional Dimensions of FICS

Figure 13:
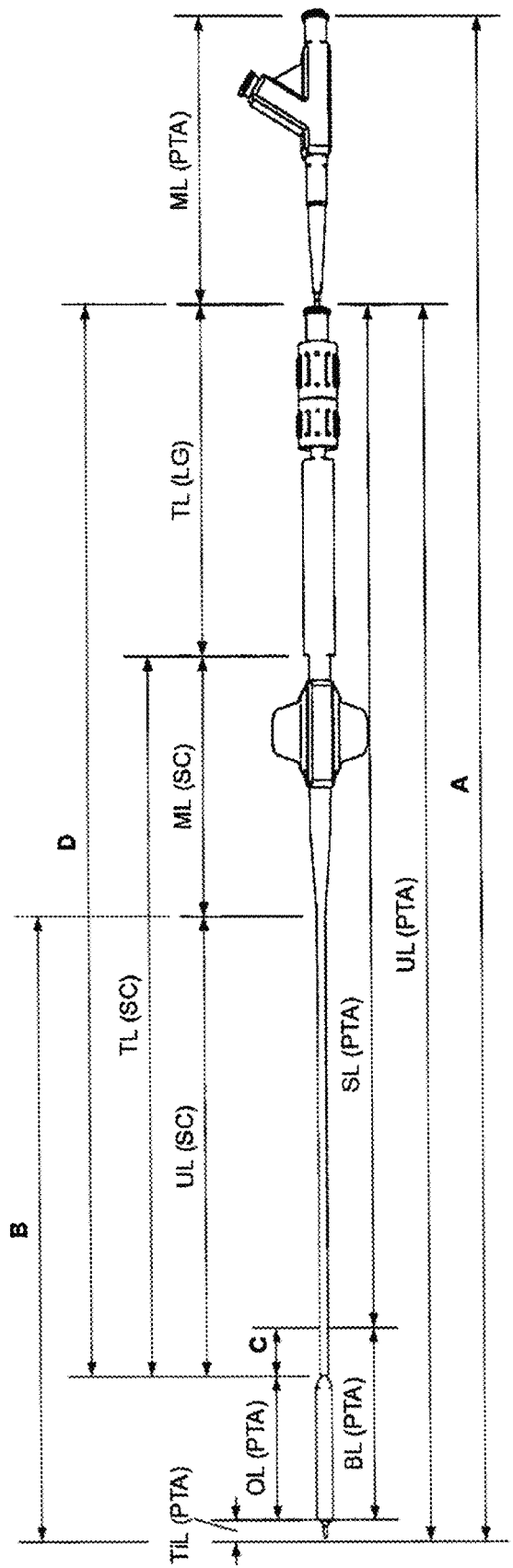
FIG. 13 is a dimensional diagram of an FICS in a fully extended LLS PTA Catheter configuration, showing the relative dimensional interoperability of the individual functional units and functional subunits.

FIG. 13 is a dimensional diagram of an FICS in a fully extended LLS PTA catheter configuration, showing the relative dimensional interoperability of the individual functional units and functional subunits. In FIG. 13, the hypothetical dimensional values for the components of the FICS LLS PTA catheter configuration are assigned with both component-specific reference abbreviations (LG, SC, PTA, DIL, and CTO) and functional dimension-specific reference abbreviations (TL, UL, ML, RL, BL, OL, SL, TiL). The functional dimension-specific reference abbreviations represent the lengths of the FICS components, as provided in Table 1 under Example 1. Furthermore, Table 2 provides formulas for calculating the functional dimensions corresponding to the components (labeled in FIG. 13; listed in Table 1). The various functional dimensions listed in the first column of Table 2 represent the operational lengths and operational relationships among the components of the functional units and "functional subunits."

In FIG. 13, the functional dimension "A" refers to the constant total length TL of the FICS, the functional dimension "B" refers to the variable usable length portion UL; the functional dimension "D" refers to the fixed total length portion of the combined total lengths of the support catheter SC and the Lock Grip LG; and the functional dimension "C" refers to a variably recessed length portion (describing the sheathed balloon length portion RL relative to the complete balloon length portion BL). The difference BL-RL defines the operational balloon length OL that can be variably adjusted between a minimum and maximum threshold, wherein the adjustable operational length is measured as the distance between the position of the radiopaque markers incorporated into the distal end of the balloon member of the PTA catheter and the position of the radiopaque markers incorporated into the distal end of the support catheter shaft.

TABLE 1

ABBREVIATIONS FOR FICS COMPONENTS

| | |
|---|---|
| TL | Total Length |
| UL | Usable Length |
| ML | Manifold Length |
| RL | Recessed Length |
| BL | Balloon Length |
| OL | Operational Balloon Length |
| SL | Shaft Length |
| TiL | Tip Length |
| (LG) | Lock Grip |
| (SC) | support catheter |
| (PTA) | PTA catheter |
| (DIL) | Dilator |
| (CTO) | CTO penetration tip |

TABLE 2

CALCULATION OF FUNCTIONAL DIMENSIONS

| Functional Dimensions | EXEMPLARY CORRELATIONS | |
|---|---|---|
| A | TL (LLS) = TL (PTA) = UL (PTA) + ML (PTA) | (constant) |
| B | UL (LLS) = UL (SC) + OL (PTA) + TiL (PTA) | (variable) |
| C | D − SL (PTA) = RL (PTA) = BL (PTA) − OL (PTA) | (variable) |
| D | TL (SC) + TL (LG) = UL (SC) + ML (SC) + TL (LG) | (constant) |
| ΔB | B (max) − B (min) = OL (max) − OL (min) | (UL Range) |
| | OL (max) = BL − C (min) | |
| | OL (min) = BL − C (max) | |
| ΔC | C (max) − C (min) | (RL Range) |
| | \|ΔB\| = \|ΔC\| | |
| | Other FICS UL per (Configuration) | |
| | UL (CTO) = UL (SC) + TiL (DIL) + OL (CTO) | |
| | UL (REENTRY) = UL (SC) + TiL (Dil) + OL (REENTRY) | |

Example 2

FICS Total Length TL (A)

The total length ("TL") refers to the total length of the FICS or individual functional units. The total length ("TL") can be derived by adding together the respective lengths of the components for the functional units and functional subunits. The relative correlations between the lengths of components for the LLS PTA configuration are provided in TABLE 2, as an example. Exemplary total length ("TL") ranges for the respective components of the FICS are provided in TABLE 3 (LLS PTA Configuration, UL 80 cm) and in TABLE 4 (LLS PTA Configuration, UL 135 cm) under Example 3 below. The TL of the FICS reentry dilator and/or the FICS CTO-dilator configuration can be derived similarly (not shown). Since the TL of the FICS LLS PTA configuration always exceeds the TL of the CTO-dilator and/or reentry-dilator configuration, the TL of the FICS LLS PTA configuration can be utilized by the physician for adequate guide-wire length selection prior to commencing the procedure.

Example 3

FICS Usable Length UL (B)

The usable length ("UL") refers to the indwelling/working length portion of the FICS or the individual functional units. The UL correlates with the distance between the access point (patient entry site) and the target-treatment point that can be reached by the FICS. The FICS can provide a range of different, predefined ULs corresponding to the respective components of the FICS for treating a broad range of complex lesions and/or CTOs. As examples, two usable lengths of respective components are provided for one therapeutic-specific configurations: the FICS LLS PTA Configuration with a UL of 80 cm (TABLE 3) and the FICS LLS PTA Configuration with a UL of 135 cm (TABLE 4). Clinically relevant access lengths correlating with the distance measurable from the most commonly used (pre-defined) patient entry points to a hypothetical target site (distance beyond a hypothetical lesion located in a pre-defined target region) are provided in TABLE 5. The usable length UL portion of the components of the FICS can be selected based on the determined access length.

It can be shown, in absolute values, that the usable length portion "B" of the FICS in the LLS PTA configuration can be adjusted in a dimensional range |ΔB| that is equivalent to the balloon extension range |ΔC|. This leads to a variable adjustability of the usable length "B" whereas the total length "A" of the FICS can remain constant. This property differs in comparison to conventional systems, wherein both usable length and total length are constant. Due to this specific configuration, the FICS in the LLS PTA configuration enables a custom length-adjustable operational balloon length that can be adapted for lesion-length-selective dilation (optionally anchoring/centering), in which the system itself can exhibit an adjustable UL portion substantially at the same time.

Other FICS configurations, such as the FICS CTO-dilator configuration and the FICS reentry-dilator configuration can exhibit variable usable length ranges, as described in TABLE 2. In the case of the FICS CTO and/or reenter configurations, the individual operational tip lengths can be added to arrive at analogous dimensional correlations referenced in TABLE 4

TABLE 3

FICS LLS PTA CATHETER CONFIGURATION, UL 80 cm

| all units [mm] | Min | Max | Opt |
|---|---|---|---|
| UL (SYSTEM) = UL (SC) | 800 | | |
| ML (SC) | 10 | 50 | 20 |
| TL (LG) | 20 | 100 | 50 |
| TiL (PTA) | 5 | 10 | 5 |
| OL (PTA) | 0 | 180 | 0-180 |
| ML (PTA) | 40 | 80 | 80 |
| TL (SYSTEM) = TL (PTA) | 875 | 1220 | 1135 |
| BL (PTA) | 10 | 200 | 200 |
| RL (PTA) | 10 | 20 | 20 |
| SL (PTA) | 820 | 930 | 850 |
| UL (PTA) | 835 | 1140 | 1055 |

TABLE 4

FICS LLS PTA CATHETER CONFIGURATION, UL 135 cm

| all units [mm] | Min | Max | Opt |
|---|---|---|---|
| UL (SYSTEM) = UL (SC) | 1350 | | |
| ML (SC) | 10 | 50 | 20 |
| TL (LG) | 20 | 100 | 50 |

TABLE 4-continued

FICS LLS PTA CATHETER CONFIGURATION, UL 135 cm

| all units [mm] | Min | Max | Opt |
|---|---|---|---|
| TiL (PTA) | 5 | 10 | 5 |
| OL (PTA) | 0 | 180 | 0-180 |
| ML (PTA) | 40 | 80 | 80 |
| TL (SYSTEM) = TL (PTA) | 1425 | 1770 | 1685 |
| BL (PTA) | 10 | 200 | 200 |
| RL (PTA) | 10 | 20 | 20 |
| SL (PTA) | 1370 | 1480 | 1400 |
| UL (PTA) | 1385 | 1690 | 1605 |

Example 4

TABLE 5

ACCESS LENGTHS (across Lesion)

| all units [cm] Target Regions | Entry Points | | | |
|---|---|---|---|---|
| | CFA ipsilateral | CFA contralateral | Brachial | Radial |
| Illiac | 1-30 | 30-60 | 70-100 | 100-130 |
| SFA | 1-30 | 30-60 | 100-130 | 130-160 |
| BTK | 50-80 | 80-110 | 150-180 | 180-210 |

CFA = common femoral artery
SFA = superficial femoral artery
BTK = below the knee FICS Compatibility with Guide-Wire Length The TL correlates with the guide-wire length needed to effectively operate all combined functional units in their respective configurations (on/over the guide wire). When planning an interventional procedure, the physician can use the total system length as an orientation for selecting an adequately sized guide wire. TABLE 6 provides a list of recommended and calculated guide-wire lengths correlating with the FICS total length (LLS PTA configuration).

TABLE 6

FICS GUIDEWIRE LENGTH COMPATIBILITY

| GW LENGTH COMPATIBILITY | | TOTAL LENGTH (A) | USABLE LENGTH (B) |
|---|---|---|---|
| (recommended) | (calc.)* | all units [mm] | |
| 4500 | 4370 | 2135 | 1800 |
| 4000 | 3970 | 1935 | 1600 |
| 3800 | 3770 | 1835 | 1500 |
| 3500 | 3470 | 1685 | 1350 |
| 3200 | 3170 | 1535 | 1200 |
| 2800 | 2770 | 1335 | 1000 |
| 2600 | 2570 | 1235 | 900 |
| 2400 | 2370 | 1135 | 800 |
| 2000 | 1970 | 935 | 600 |

*GW LENGTH COMPATIBILITY = [(SYSTEM TL (MAX) * 2) + 100]

Example 5

FICS Guide-Wire Diameter Compatibility

The phrase "guide wire compatibility" refers to a minimum inner diameter (ID) of the lumen of a functional unit/instrument for passing a guidewire of certain outer diameter without resistance. Guide wire compatibility is governed by the guide-wire lumen ID of each insertable functional unit, for example, the guide-wire-lumen ID of the dilator, the PTA catheter, or respectively the lumen ID of the hypotube coaxially incorporated in the dilator tip design as utilized in the CTO-dilator and/or reentry-dilator configurations. Guide wires can typically be offered with outer diameter ranges between 0.014-0.035 [in], equivalent to 0.356-0.889 [mm]. The functional units of the FICS, particularly the PTA catheter, dilator and hypotube component can be configured to be 0.018 in./0.457 mm compatible. Other dimensions and ranges can be contemplated for different clinical applications.

Example 6

FICS Introducer Sheath Compatibility

The phrase "sheath compatibility" refers to the maximum instrument outer diameter (OD) along the UL that can be introduced through an introducer sheath of commensurate inner diameter without resistance. The components of the FICS can be dimensionally configured based on the relative diameters of the components. The FICS can be designed to pass through the inner diameter of introducer sheaths having a variable range. Thus, the outer diameter along the usable length portion of the FICS can be configured to be receivable through an introducer sheath having a compatible inner diameter. For example, TABLE 7 provides the dimensions of a PTA balloon member (widths and lengths) that may be recommended for obtaining sheath compatibility suitable for the FICS LLS PTA configuration, wherein the PTA catheters having balloon diameters that can range between 2.0-7.0 mm, for example. The operational balloon length OL (Table 7) can be adjusted through the interoperation of the SC, the LG and the PTA functional units as described in FIG. 12. The balloon length BL of the Dilator and the PTA catheter can be configured within a fixed range as described in TABLES 3-4. Other dimensions and ranges can be contemplated for different clinical applications. For example, a system for retrograde pedal/tibial access can be dimensioned using a sheath compatible at 3Fr. For the FICS CTO-dilator configuration, the proximal maximum outer diameter of a polymeric tip (e.g., refer to FIGS. 6-7, components 620/720) can correspond to the minimum inner diameter of the lumen of FICS support catheter, for example, ranging between 3.0-4.0 Fr.

TABLE 7

FICS SHEATH COMPATIBILITY

| Balloon Diameter | Operational Balloon Length [mm] | | | | | | | |
|---|---|---|---|---|---|---|---|---|
| [mm] | 20 | 40 | 60 | 80 | 100 | 120 | 150 | 180 |
| 2.0 | 4Fr | 4Fr | 4Fr | 4Fr | 4Fr | 4Fr | 4Fr | 4Fr |
| 2.5 | 4Fr | 4Fr | 4Fr | 4Fr | 4Fr | 4Fr | 4Fr | 4Fr |
| 3.0 | 4Fr | 4Fr | 4Fr | 4Fr | 4Fr | 4Fr | 4Fr | 4Fr |
| 3.5 | 4Fr | 4Fr | 4Fr | 4Fr | 4Fr | 4Fr | 4Fr | 4Fr |
| 4.0 | 5Fr | 5Fr | 5Fr | 5Fr | 5Fr | 5Fr | 5Fr | 5Fr |
| 5.0 | 5Fr | 5Fr | 5Fr | 5Fr | 5Fr | 5Fr | 5Fr | 5Fr |
| 6.0 | 5Fr | 5Fr | 5Fr | 5Fr | 5Fr | 5Fr | 5Fr | 5Fr |
| 7.0 | 5Fr | 5Fr | 5Fr | 5Fr | 5Fr | 5Fr | 5Fr | 5Fr |

Note:
1 [Fr] = 0.333 [mm]

The foregoing description, for purposes of explanation, refers to specific nomenclature to provide a thorough understanding of the invention. However, it will be apparent to one skilled in the art that the specific details are not required in order to practice the invention. The foregoing descriptions of specific embodiments of the present invention are presented for purpose of illustration and description. They are not intended to be exhaustive or to limit the invention to the precise forms disclosed. Many modifications and variations are possible in view of the above teachings. The embodiments are shown and described in order to best explain the principles of the invention and practical applications, to thereby enable others skilled in the art to best utilize the invention and various embodiments with various modifications as suitable for the particular uses contemplated. It is intended that the scope of the invention be defined by the following claims and their equivalent.

The invention claimed is:

1. A catheter system comprising:
   at least one support catheter that includes a support-catheter shaft member with a support-catheter lumen and a support-catheter manifold that provides fluid communication to the support-catheter lumen,
   at least one dilator that includes a dilator tip, a dilator shaft member with one or more dilator lumens, and a dilator manifold that provides fluid communication to one or more of the one or more dilator lumens, the dilator shaft member having an external diameter that allows the dilator shaft member to be inserted into the support-catheter lumen of the at least one support catheter, and
   at least one percutaneous transluminal angioplasty ("PTA") catheter that includes an inflatable member attached to a PTA-catheter shaft member with two or more PTA-catheter lumens, and a PTA-catheter manifold that provides fluid communication to one or more of the two or more PTA-catheter lumens, the PTA-catheter shaft member having an external diameter that allows the PTA-catheter shaft member to be inserted into the support-catheter lumen of each of the at least one support catheter; and
   a lock-grip handle having a lock-grip-handle body and a lock-grip-handle seal, the lock-grip handle being coupled at a proximal, non-indwelling shaft portion of the at least one support catheter, the lock grip handle seal being configured to inhibit fluid communication to an enclosed volume between an inner surface of the lumen of the at least one support catheter and an external surface of the dilator shaft member or an external surface of the PTA-catheter shaft member when the dilator shaft member or the PTA-catheter shaft member is inserted through the lock-grip handle and into the lumen of the support catheter.

2. The catheter system of claim 1 wherein the lock-grip handle additionally comprises an actuator that stores and releases mechanical energy to facilitate advancement and retraction of the dilator shaft member or the PTA-catheter shaft member.

3. The catheter system of claim 1 wherein the dilator tip included in the at least one dilator is selected from a number of different types of dilator tips that include:
   chronic-total-occlusion-penetration dilator tips used for intraluminal recanalization; and
   reentry dilator tips used for extraluminal circumnavigation of a chronic total occlusion.

4. The catheter system of claim 1 wherein the inflatable member of the at least one PTA catheter has a specific length, diameter, and compliance.

5. The catheter system of claim 1 wherein, when the at least one PTA catheter is inserted into the at least one support catheter, a specific portion of the inflatable member of a defined length can be extended past a distal end of the at least one support catheter so that, when an inflation fluid is introduced through an inflation port of the PTA-catheter manifold, only the portion of the inflatable member extended past the distal end of the at least one support catheter is inflated.

6. The catheter system of claim 1, wherein the lock-grip-handle seal forms a hemostatic seal against the at least one support catheter.

7. The catheter system of claim 1, wherein the lock-grip handle seal is compressible.

8. The catheter system of claim 1, wherein the lock-grip-handle comprises a hemostatic valve.

9. The catheter system of claim 1, wherein the inflatable member is a balloon, and the balloon is configured to be inflated to variable lengths.

10. The catheter system of claim 1, wherein the lock-grip handle comprises a lower cam body, the catheter system comprising a hypotube mechanically coupled to the lower cam body by the lock-grip handle seal, the seal being configured to be compressed.

11. The catheter system of claim 1, wherein the inflatable member comprises a balloon, wherein the lock-grip handle is configured to stabilize a position of the at least one PTA catheter by preventing recession of the at least one support catheter during a dilatation of the balloon.

12. The catheter system of claim 11, wherein a portion of the balloon is configured to be maintained within a distal end of the at least one support catheter during inflation and deflation of a remaining portion of the balloon.

13. The catheter system of claim 11, wherein the lock-grip handle comprises a mechanical end stop, limiting a longitudinal displacement of the dilator shaft member, the dilator tip, and/or a proximal balloon cone.

14. The catheter system of claim 1, wherein the inflatable member comprises a portion of constant length configured to be concentrically concealed within the at least one support catheter.

15. The catheter system of claim 1, comprising a mechanical actuation mechanism dimensionally configurable to co-axially accommodate the at least one dilator to enhance positional control over the dilator tip or the at least one PTA catheter to enhance an extension range of the inflatable member.

16. The catheter system of claim 1, comprising a dilator tip propagation mechanism configured to be connected to a proximal end of the at least one support catheter member and configured such that two different positions of the dilator tip can be mechanically actuated by loading or releasing tension on a co-axially positioned spring member.

17. The catheter system of claim 1, comprising a combined tip-propagation mechanism and a shaft-locking mechanism configured to independently facilitate hemostatic sealing, mechanical locking, and tip extension at substantially the same or different time points.

18. The catheter system of claim 1, comprising a spring mechanism configured to mechanically control translation of the at least one PTA catheter with each incremental distance of a dilator tip propagation being triggered by an incremental compression of the spring mechanism, resulting in an incremental exposure of a portion of the inflatable member.

19. The catheter system of claim 1, comprising a hemostatic valve connected to a proximal end of the at least one support catheter.

20. The catheter system of claim 1, wherein the lock-grip handle is configured as a displacement and locking element.

21. The catheter system of claim 1, comprising multiple radiopaque markings at the distal end of one or both of the at least support catheter shaft and a distal end of the inflatable member configured to provide visual guidance for determining a length of the inflatable member exposed from the support catheter.

22. The catheter system of claim 1, wherein the at least one support catheter comprises a visual marking identifying an inflation length of the balloon.

* * * * *